US008642550B2

(12) United States Patent
Dickey et al.

(10) Patent No.: US 8,642,550 B2
(45) Date of Patent: Feb. 4, 2014

(54) CHIMERIC NATRIURETIC PEPTIDES WITHOUT HYPOTENSIVE INDUCING CAPABILITY

(75) Inventors: Deborah Dickey, Minneapolis, MN (US); John C. Burnett, Jr., Rochester, MN (US); Lincoln R. Potter, Roseville, MN (US)

(73) Assignees: Mayo Foundation for Medical Education and Research, Rochester, MN (US); Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 13/125,772

(22) PCT Filed: Oct. 21, 2009

(86) PCT No.: PCT/US2009/061511
§ 371 (c)(1),
(2), (4) Date: Aug. 3, 2011

(87) PCT Pub. No.: WO2010/048308
PCT Pub. Date: Apr. 29, 2010

(65) Prior Publication Data
US 2011/0282030 A1    Nov. 17, 2011

Related U.S. Application Data

(60) Provisional application No. 61/108,423, filed on Oct. 24, 2008.

(51) Int. Cl.
*C07K 14/00* (2006.01)
*A61K 38/22* (2006.01)
(52) U.S. Cl.
USPC .......................................... 514/12.4; 530/324
(58) Field of Classification Search
None
See application file for complete search history.

(56) References Cited

U.S. PATENT DOCUMENTS

| | | | | |
|---|---|---|---|---|
| 4,034,074 | A | 7/1977 | Miles | |
| 4,098,876 | A | 7/1978 | Piasio et al. | |
| 4,233,402 | A | 11/1980 | Maggio et al. | |
| 5,296,347 | A | 3/1994 | LaMotte, III | |
| 5,580,859 | A | 12/1996 | Felgner et al. | |
| 5,583,108 | A | 12/1996 | Wei et al. | |
| 5,589,466 | A | 12/1996 | Felgner et al. | |
| 6,407,211 | B1 * | 6/2002 | Burnett et al. | 530/350 |
| 7,384,917 | B2 * | 6/2008 | Burnett et al. | 514/12.4 |

FOREIGN PATENT DOCUMENTS

WO    WO 2007/035600    3/2007

OTHER PUBLICATIONS

Dickey et al., Novel Bifunctional Natriuretic Peptides as Potential Therapeutics, J. Biological Chemistry, 283, 35003-35009, 2008.*
Wells JA, Additivity of mutational effects in proteins., Biochemistry, vol. 29, pp. 8509-8517, 1990.*
Abbey and Potter, "Vasopressin-dependent Inhibition of the C-type Natriuretic Peptide Receptor, NPR-B/GC-B, Requires Elevated Intracellular Calcium Concentrations," *J. Biol. Chem.*, 2002, 277(45):42423-42430.
Ausubel et al., Ed, "Immunology," *Short Protocols in Molecular Biology*, Chapter 11, Green Publishing Associates and John Wiley & Sons, 1992.
Ausubel et al., Ed., "Mutagensis of Cloned DNA," *Short Protocols in Molecular Biology*, Chapter 8, Green Publishing Associates and John Wiley & Sons, 1992.
Bryan et al., "Renal hyporesponsiveness to atrial natriuretic peptide in congestive heart failure results from reduced atrial natriuretic peptide receptor concentrations," *Am. J. Phys. Renal. Phys.*, 2007, 292(5):F1636-1644.
Chaurand et al., "Peptide and Protein Identification by Matrix-Assisted Laser Desorption Ionization (MALDI) and MALDI-Post-Source Decay Time-of-Flight Mass Spectrometry," *J. Am. Soc. Mass Spectrom.*, 1999, 10(2):91-103.
Cole et al., "The EBV-Hybridoma Technique and As Application to Human Lung Cancer," *Monoclonal Antibodies and Cancer Therapy*, Alan R. Liss, Inc., pp. 77-96, 1983.
Cote et al., Generation of human monoclonal antibodies reactive with cellular antigens,' *Proc. Natl. Aca. Sci. USA*, 1983, 80:2026.
Cunningham et al., "Production of an Atrial Natriuretic Peptide Variant that is Specific for Type A Receptor," *Embo J*, 1994, 13(11):2508-2515.
Currie et al., "Purification and sequence analysis of bioactive atrial peptides," *Science*, 1984, 223(4631):67-69.
Dickey et al., "Differential Regulation of Membrane Guanylyl Cyclases in Congestive Heart Failure: Natriuretic Peptide Receptor (NPR)-B, Not NPR-A, is the Predominant Natriuretic Peptide Receptor in the Failing Heart," *Endocrinology*, 2007, 148(7):3518-3522.
Gevaert et al., "Protein identification based on matrix assisted laser desorption/ionization-post source decay-mass spectrometry," *Electrophoresis*, 2001, 22(9):1645-1651.
Guatelli et al., "Isothermal, *in vitro* amplification of nucleic acids by a multienzyme reaction modeled after retroviral replication," *Proc. Natl. Acad. Sci USA*, 1990, 87:1874-1878.
Huse et al., "Generation of a Large Combinatorial Library of the Immunoglobulin Repertoire in Phage Lambda," *Science*, 1989, 246:1275-1281.
Hyrup et al., "Peptide Nucleic Acids (PNA): Synthesis, Properties and Potential Applications," *Bioorgan. Med. Chem.*, 1996, 4:5-23.
Johns et al., "*Dendroaspis* natriuretic peptide binds to the natriuretic peptide clearance receptor," *Biochem. Biophys. Res. Comm.*, 2007, 358(1):145-149.

(Continued)

Primary Examiner — Elly-Gerald Stoica
(74) Attorney, Agent, or Firm — Fish & Richardson P.C.

(57) ABSTRACT

This document provides natriuretic polypeptides. For example, this document provides polypeptides having a natriuretic activity. In some cases, a polypeptide provided herein can have natriuretic activities without lowering blood pressure. Methods and materials for inducing natriuretic activities within a mammal also are provided.

9 Claims, 10 Drawing Sheets

(56) References Cited

OTHER PUBLICATIONS

Kohler et al., "Continuous cultures of fused cells secreting antibody of predefined specificity," *Nature*, 1975, 256:495-497.

Kozbor et al., "The production of monoclonal antibodies from human lymphocytes," *Immunology Today*, 1983, 4(3):72-79.

Langenickel et al., "Cardiac hypertrophy in transgenic rats expressing a dominant-negative mutant of the natriuretic peptide receptor B," *Proc Natl Acad Sci USA*, 2006, 103(12):4735-4740.

Lewis, "PCR's Competitors are Alive and Well and Moving Rapidly Towards Commercialization," *Genetic Engineering News*, 1992, 12(9):1.

Lisy et al., "Therapeutic Actions of a New Synthetic Vasoactive and Natriuretic Peptide, Dendroaspis Natriuretic Peptide, in Experimental Severe Congestive Heart Failure," *Hypertension*, 2001, 37(4):1089-1094.

Misono et al., "Rat atrial natriuretic factor: Isolation, structure and biological activities of four major peptides," *Biochem Biophy Res Commun*, 1984, 123(2):444-451.

Ogawa et al., "Crystal Structure of Hormone-bound Atrial Natriuretic Peptide Receptor Extracellular Domain," *J Biol Chem*, 2004, 279(27):28625-28631.

Potter et al., "Natriuretic Peptides, Their Receptors, and Cyclic Guanosine Monophosphate-Dependent Signaling Functions," *Endocr Rev.*, 2006, 27(1):47-72.

Rose and Giles, "Natriuretic peptide C receptor signaling in the heart and vasculature," *J Physiol*, 2008, 586(2):353-366.

Sackner-Bernstein et al., "Risk of Worsening Renal Function with Nesiritide in Patients with Acutely Decompensated Heart Failure," *Ciruclation*, 2005, 111(12):1487-1491.

Scarborough et al., "Truncated atrial natriuretic peptide analogs. Comparison between receptor binding and stimulation of cyclic GMP accumulation in cultured vascular smooth muscle cells," *J Biol Chem*, 1986, 261(28):12960-12964.

Schoenfeld et al., "Agonist selectivity for three species of natriuretic peptide receptor-A," *Mol Pharmacol*, 1995, 47(1):172-180.

Singh et al., "Novel Snake Venom Ligand Dendroaspis Natriuretic Peptide is Selective for Natriuretic Peptide Receoptor-A in Human Heart," *Circ Res*, 2006, 99(2):183-190.

Soeki et al., "C-type natriuretic peptide, a novel antifibrotic and antihypertrophic agent, prevents cardiac remodeling after myocardial infarction," *J Am Coll Cardiol*, 2005, 45(4):608-616.

Summerton and Weller, "Morpholino Antisense Oligomers: Design, Preparation, and Properties," *Antisense Nucleic Acid Drug Dev.*, 1997, 7:187-195.

Wei et al., "Action of C-type natriuretic peptide in isolated canine arteries 1993, 264(1 Pt 2):H71-73 and veins," *Am J Physiol*, 1993, 264(1 Pt 2):H71-73.

Weiss, "Hot Prospect for New Gene Amplifier," *Science*, 1991, 254:1292-1293.

International Preliminary Report on Patentability in Application No. PCT/US2009/061511, mailed Apr. 26, 2011, 6 pages.

International Search Report and Written Opinion in Application No. PCT/US2009/061511, mailed Jul. 5, 2010, 12 pages.

\* cited by examiner

| | | | |
|---|---|---|---|
| Human ANP (1-28) | | SLRRSSCFGGRMDRIGAQSGLGCNSFRY | |
| Human BNP (1-32) | SPKMVQGSGCFGRKMDRISSSSGLGCKVLRRH | | |
| CNP (1-22) | | GLSKGCFGLKLDRIGSMSGLGC | |
| DNP (1-38) | | EVKYDPCFGHKIDRINHVSNLGCPSLRDPRPNAPSTSA | |
| CD-NP (1-37) | | GLSKGCFGLKLDRIGSMSGLGCPSLRDPRPNAPSTSA | |
| c-terminal peptide (1-15) | | PSLRDPRPNAPSTSA | |
| B-CDNP (1-37) | | GLSKGCFGRKMDRIGSMSGLGCPSLRDPRPNAPSTSA | |
| CDNP-B (1-37) | | GLSKGCFGLKLDRISSSSGLGCPSLRDPRPNAPSTSA | |

FIG. 3

SEQUENCE LISTING

<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: synthetically generated peptide

<400> SEQUENCE: 1

Gly Leu Ser Lys Gly
 1               5

<210> SEQ ID NO 2
<211> LENGTH: 18
<212> TYPE: PRT
<213> ORGANISM: Artificial Sequence
<220> FEATURE:
<223> OTHER INFORMATION: synthetically generated peptide

<400> SEQUENCE: 2

Cys Phe Gly Arg Lys Met Asp Arg Ile Gly Ser Met Ser Gly Leu Gly
 1               5                  10                  15

Cys Pro

<210> SEQ ID NO 3
<211> LENGTH: 14
<212> TYPE: PRT
<213> ORGANISM: Artificial Sequence
<220> FEATURE:
<223> OTHER INFORMATION: synthetically generated peptide

<400> SEQUENCE: 3

Ser Leu Arg Asp Pro Arg Pro Asn Ala Pro Ser Thr Ser Ala
 1               5                  10

<210> SEQ ID NO 4
<211> LENGTH: 37
<212> TYPE: PRT
<213> ORGANISM: Artificial Sequence
<220> FEATURE:
<223> OTHER INFORMATION: synthetically generated peptide

<400> SEQUENCE: 4

Gly Leu Ser Lys Gly Cys Phe Gly Arg Lys Met Asp Arg Ile Gly Ser
 1               5                  10                  15

Met Ser Gly Leu Gly Cys Pro Ser Leu Arg Asp Pro Arg Pro Asn Ala
                20                  25                  30

Pro Ser Thr Ser Ala
            35

<210> SEQ ID NO 5
<211> LENGTH: 37
<212> TYPE: PRT
<213> ORGANISM: Artificial Sequence
<220> FEATURE:
<223> OTHER INFORMATION: synthetically generated peptide

<400> SEQUENCE: 5

Gly Leu Ser Lys Gly Cys Phe Gly Leu Lys Leu Asp Arg Ile Ser Ser
 1               5                  10                  15

Ser Ser Gly Leu Gly Cys Pro Ser Leu Arg Asp Pro Arg Pro Asn Ala
                20                  25                  30

```
Pro Ser Thr Ser Ala
        35

<210> SEQ ID NO 6
<211> LENGTH: 18
<212> TYPE: PRT
<213> ORGANISM: Artificial Sequence
<220> FEATURE:
<223> OTHER INFORMATION: synthetically generated peptide

<400> SEQUENCE: 6

Cys Phe Gly Leu Lys Leu Asp Arg Ile Ser Ser Ser Gly Leu Gly
 1               5                  10                  15

Cys Pro

<210> SEQ ID NO 7
<211> LENGTH: 37
<212> TYPE: PRT
<213> ORGANISM: Artificial Sequence
<220> FEATURE:
<223> OTHER INFORMATION: synthetically generated peptide

<400> SEQUENCE: 7

Gly Leu Ser Lys Gly Cys Phe Gly Leu Lys Leu Asp Arg Ile Gly Ser
 1               5                  10                  15

Met Ser Gly Leu Gly Cys Pro Ser Leu Arg Asp Pro Arg Pro Asn Ala
                20                  25                  30

Pro Ser Thr Ser Ala
        35
```

CHIMERIC NATRIURETIC PEPTIDES WITHOUT HYPOTENSIVE INDUCING CAPABILITY

CROSS-REFERENCE TO RELATED APPLICATIONS

This application is a National Stage application under 35 U.S.C. 371 and claims benefit under 35 U.S.C. 119(a) of International Application No. PCT/US2009/061511, having an International Filing Date of Oct. 21, 2009, which claims the benefit of priority from U.S. Provisional Application Ser. No. 61/108,423, filed on Oct. 24, 2008. The disclosures of the prior applications are considered part of (and are incorporated by reference in) the disclosure of this application.

BACKGROUND

1. Technical Field

This document relates to natriuretic polypeptides. For example, this document provides methods and materials related to natriuretic polypeptides and the use of natriuretic polypeptides to treat cardiovascular and renal conditions.

2. Background Information

Natriuretic polypeptides are polypeptides that can cause natriuresis (increased sodium excretion in the urine). Such polypeptides can be produced by brain, heart, kidney, and/or vasculature tissue.

SUMMARY

This document relates to natriuretic polypeptides. For example, this document provides methods and materials related to natriuretic polypeptides and the use of natriuretic polypeptides to treat cardiovascular conditions, renal conditions, or both cardiovascular conditions and renal conditions. In some cases, a polypeptide provided herein can have diuretic activity, natriuretic activity, the ability to activate cGMP, the ability to increase glomerular filtration rate, the ability to reduce renin production, the ability to reduce angiotensin production, the ability to reduce aldosterone production, the ability to reduce abnormally elevated cardiac filling pressures, the ability to optimize renal blood flow, or a combination thereof. In some cases, a polypeptide provided herein can increase endogenous ANP, BNP, and CNP levels. In some cases, a polypeptide provided herein can lack the ability to lower blood pressure and can lack the ability to cause systemic hypotension. In some cases, a polypeptide provided herein can be an agonist for natriuretic peptide receptor-A, natriuretic peptide receptor-B, or both natriuretic peptide receptor-A and natriuretic peptide receptor-B.

In general, one aspect of this document features a polypeptide less than 44 amino acid residues in length, wherein the polypeptide comprises or consists essentially of, in an order from amino terminus to carboxy terminus:

(a) the sequence set forth in SEQ ID NO:1 or the sequence set forth in SEQ ID NO:1 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:3 or the sequence set forth in SEQ ID NO:3 with no more than three additions, subtractions, or substitutions, but which polypeptide is not a CD-NP polypeptide. A CD-NP polypeptide has the following amino acid sequence: Gly-Leu-Ser-Lys-Gly-Cys-Phe-Gly-Leu-Lys-Leu-Asp-Arg-Ile-Gly-Ser-Met-Ser-Gly-Leu-Gly-Cys-Pro-Ser-Leu-Arg-Asp-Pro-Arg-Pro-Asn-Ala-Pro-Ser-Thr-Ser-Ala (SEQ ID NO:7). The polypeptide can comprise natriuretic activity. The polypeptide can comprise a cGMP-activating property. The polypeptide can comprise a natriuretic and diuretic activity. The polypeptide can comprise a cardiac-unloading activity. The polypeptide can comprise an RAAS-suppressing activity. The polypeptide can lack the ability to induce systemic hypotension. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise or consist essentially of the sequence set forth in SEQ ID NO:1, the sequence set forth in SEQ ID NO:2, and the sequence set forth in SEQ ID NO:3. The polypeptide can comprise the sequence set forth in SEQ ID NO:1 with no more than three conservative amino acid substitutions (e.g., three, two, one, or no conservative amino acid substitutions). The polypeptide can comprise the sequence set forth in SEQ ID NO:2 with no more than five conservative amino acid substitutions (e.g., five, four, three, two, one, or no conservative amino acid substitutions). The polypeptide can comprise the sequence set forth in SEQ ID NO:3 with no more than three conservative amino acid substitutions (e.g., three, two, one, or no conservative amino acid substitutions). The polypeptide can be a substantially pure polypeptide.

In another aspect, this document features a polypeptide less than 44 amino acid residues in length, wherein the polypeptide comprises or consists essentially of, in an order from amino terminus to carboxy terminus:

(a) the sequence set forth in SEQ ID NO:1 or the sequence set forth in SEQ ID NO:1 with no more than three additions, subtractions, or substitutions, (b) the sequence set forth in SEQ ID NO:6 or the sequence set forth in SEQ ID NO:6 with no more than five additions, subtractions, or substitutions, and (c) the sequence set forth in SEQ ID NO:3 with no more than three additions, deletions, or substitutions, but which polypeptide is not a CD-NP polypeptide (SEQ ID NO:7). The polypeptide can comprise natriuretic activity. The polypeptide can comprise a cGMP-activating property. The polypeptide can comprise a natriuretic and diuretic activity. The polypeptide can comprise a cardiac-unloading activity. The polypeptide can comprise an RAAS-suppressing activity. The polypeptide can lack the ability to induce systemic hypotension. The polypeptide can comprise the sequence set forth in SEQ ID NO:1. The polypeptide can comprise the sequence set forth in SEQ ID NO:6. The polypeptide can comprise the sequence set forth in SEQ ID NO:3. The polypeptide can comprise the sequence set forth in SEQ ID NO:1 with no more than three conservative amino acid substitutions (e.g., three, two, one, or no conservative amino acid substitutions). The polypeptide can comprise the sequence set forth in SEQ ID NO:6 with no more than five conservative amino acid substitutions (e.g., five, four, three, two, one, or no conservative amino acid substitutions). The polypeptide can comprise the sequence set forth in SEQ ID NO:3 with no more than three conservative amino acid substitutions (e.g., three, two, one, or no conservative amino acid substitutions). The polypeptide can be a substantially pure polypeptide.

In another aspect, this document features an isolated nucleic acid encoding a polypeptide less than 44 amino acid residues in length, wherein the polypeptide comprises or consists essentially of, in an order from amino terminus to carboxy terminus:

(a) the sequence set forth in SEQ ID NO:1 or the sequence set forth in SEQ ID NO:1 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:3 or the sequence set forth in SEQ ID NO:3 with no more than three additions, subtractions, or substitutions, but which polypeptide is not a CD-NP polypeptide (SEQ ID NO:7). The polypeptide can comprise natriuretic activity. The polypeptide can comprise a cGMP-activating property. The polypeptide can comprise a natriuretic and diuretic activity. The polypeptide can comprise a cardiac-unloading activity. The polypeptide can comprise an RAAS-suppressing activity. The polypeptide can lack the ability to induce systemic hypotension. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise or consist essentially of the sequence set forth in SEQ ID NO:1, the sequence set forth in SEQ ID NO:2, and the sequence set forth in SEQ ID NO:3. The polypeptide can comprise the sequence set forth in SEQ ID NO:1 with no more than three conservative amino acid substitutions (e.g., three, two, one, or no conservative amino acid substitutions). The polypeptide can comprise the sequence set forth in SEQ ID NO:2 with no more than five conservative amino acid substitutions (e.g., five, four, three, two, one, or no conservative amino acid substitutions). The polypeptide can comprise the sequence set forth in SEQ ID NO:3 with no more than three conservative amino acid substitutions (e.g., three, two, one, or no conservative amino acid substitutions).

In another aspect, this document features an isolated nucleic acid encoding a polypeptide less than 44 amino acid residues in length, wherein the polypeptide comprises or consists essentially of, in an order from amino terminus to carboxy terminus:

(a) the sequence set forth in SEQ ID NO:1 or the sequence set forth in SEQ ID NO:1 with no more than three additions, subtractions, or substitutions, (b) the sequence set forth in SEQ ID NO:6 or the sequence set forth in SEQ ID NO:6 with no more than five additions, subtractions, or substitutions, and (c) the sequence set forth in SEQ ID NO:3 or the sequence set forth in SEQ ID NO:3 with no more than three additions, subtractions, or substitutions, but which polypeptide is not a CD-NP polypeptide (SEQ ID NO:7). The polypeptide can comprise natriuretic activity. The polypeptide can comprise a cGMP-activating property. The polypeptide can comprise a natriuretic and diuretic activity. The polypeptide can comprise a cardiac-unloading activity. The polypeptide can comprise an RAAS-suppressing activity. The polypeptide can lack the ability to induce systemic hypotension. The polypeptide can comprise the sequence set forth in SEQ ID NO:1. The polypeptide can comprise the sequence set forth in SEQ ID NO:6. The polypeptide can comprise the sequence set forth in SEQ ID NO:3. The polypeptide can comprise the sequence set forth in SEQ ID NO:1 with no more than three conservative amino acid substitutions (e.g., three, two, one, or no conservative amino acid substitutions). The polypeptide can comprise the sequence set forth in SEQ ID NO:6 with no more than five conservative amino acid substitutions (e.g., five, four, three, two, one, or no conservative amino acid substitutions). The polypeptide can comprise the sequence set forth in SEQ ID NO:3 with no more than three conservative amino acid substitutions (e.g., three, two, one, or no conservative amino acid substitutions).

In another aspect, this document features a vector comprising or consisting essentially of a nucleic acid encoding a polypeptide less than 44 amino acid residues in length, wherein the polypeptide comprises or consists essentially of, in an order from amino terminus to carboxy terminus:

(a) the sequence set forth in SEQ ID NO:1 or the sequence set forth in SEQ ID NO:1 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:3 or the sequence set forth in SEQ ID NO:3 with no more than three additions, subtractions, or substitutions, but which polypeptide is not CD-NP polypeptide (SEQ ID NO:7). The polypeptide can comprise natriuretic activity. The polypeptide can comprise a cGMP-activating property. The polypeptide can comprise a natriuretic and diuretic activity. The polypeptide can comprise a cardiac-unloading activity. The polypeptide can comprise an RAAS-suppressing activity. The polypeptide can lack the ability to induce systemic hypotension. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise or consist essentially of the sequence set forth in SEQ ID NO:1, the sequence set forth in SEQ ID NO:2, and the sequence set forth in SEQ ID NO:3. The polypeptide can comprise the sequence set forth in SEQ ID NO:1 with no more than three conservative amino acid substitutions (e.g., three, two, one, or no conservative amino acid substitutions). The polypeptide can comprise the sequence set forth in SEQ ID NO:2 with no more than five conservative amino acid substitutions (e.g., five, four, three, two, one, or no conservative amino acid substitutions). The polypeptide can comprise the sequence set forth in SEQ ID NO:3 with no more than three conservative amino acid substitutions (e.g., three, two, one, or no conservative amino acid substitutions).

In another aspect, this document features a vector comprising or consisting essentially of a nucleic acid encoding a polypeptide less than 44 amino acid residues in length, wherein the polypeptide comprises or consists essentially of, in an order from amino terminus to carboxy terminus:

(a) the sequence set forth in SEQ ID NO:1 or the sequence set forth in SEQ ID NO:1 with no more than three additions, subtractions, or substitutions, (b) the sequence set forth in SEQ ID NO:6 or the sequence set forth in SEQ ID NO:2 with no more than five additions, subtractions, or substitutions, and (c) the sequence set forth in SEQ ID NO:3 or the sequence set forth in SEQ ID NO:3 with no more than three additions, subtractions, or substitutions, but which polypeptide is not a CD-NP polypeptide (SEQ ID NO:7). The polypeptide can comprise natriuretic activity. The polypeptide can comprise a cGMP-activating property. The polypeptide can comprise a natriuretic and diuretic activity. The polypeptide can comprise a cardiac-unloading activity. The polypeptide can comprise an RAAS-suppressing activity. The polypeptide can lack the ability to induce systemic hypotension. The polypeptide can comprise the sequence set forth in SEQ ID NO:1. The polypeptide can comprise the sequence set forth in SEQ ID NO:6. The polypeptide can comprise the sequence set forth in SEQ ID NO:3. The polypeptide can comprise the sequence set forth in SEQ ID NO:1 with no more than three conservative amino acid substitutions (e.g., three, two, one, or no conservative amino acid substitutions). The polypeptide can comprise the sequence set forth in SEQ ID NO:6 with no more than five conservative amino acid substitutions (e.g., five, four, three, two, one, or no conservative amino acid substitutions). The polypeptide can comprise the sequence set forth in SEQ ID NO:3 with no more than three conservative amino acid substitutions (e.g., three, two, one, or no conservative amino acid substitutions).

In another aspect, this document features a host cell comprising a nucleic acid encoding a polypeptide less than 44 amino acid residues in length, wherein the polypeptide comprises or consists essentially of, in an order from amino terminus to carboxy terminus:

(a) the sequence set forth in SEQ ID NO:1 or the sequence set forth in SEQ ID NO:1 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:3 or the sequence set forth in SEQ ID NO:3 with no more than three additions, subtractions, or substitutions, but which polypeptide is not a CD-NP polypeptide (SEQ ID NO:7). The polypeptide can comprise natriuretic activity. The polypeptide can comprise a cGMP-activating property. The polypeptide can comprise a natriuretic and diuretic activity. The polypeptide can comprise a cardiac-unloading activity. The polypeptide can comprise an RAAS-suppressing activity. The polypeptide can lack the ability to induce systemic hypotension. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise or consist essentially of the sequence set forth in SEQ ID NO:1, the sequence set forth in SEQ ID NO:2, and the sequence set forth in SEQ ID NO:3. The polypeptide can comprise the sequence set forth in SEQ ID NO:1 with no more than three conservative amino acid substitutions (e.g., three, two, one, or no conservative amino acid substitutions). The polypeptide can comprise the sequence set forth in SEQ ID NO:2 with no more than five conservative amino acid substitutions (e.g., five, four, three, two, one, or no conservative amino acid substitutions). The polypeptide can comprise the sequence set forth in SEQ ID NO:3 with no more than three conservative amino acid substitutions (e.g., three, two, one, or no conservative amino acid substitutions). The host cell can be a eukaryotic host cell.

In another aspect, this document features a host cell comprising a nucleic acid encoding a polypeptide less than 44 amino acid residues in length, wherein the polypeptide comprises or consists essentially of, in an order from amino terminus to carboxy terminus:

(a) the sequence set forth in SEQ ID NO:1 or the sequence set forth in SEQ ID NO:1 with no more than three additions, subtractions, or substitutions, (b) the sequence set forth in SEQ ID NO:6 or the sequence set forth in SEQ ID NO:6 with no more than five additions, subtractions, or substitutions, and (c) the sequence set forth in SEQ ID NO:3 or the sequence set forth in SEQ ID NO:3 with no more than three additions, subtractions, or substitutions, but which polypeptide is not a CD-NP polypeptide (SEQ ID NO:7). The polypeptide can comprise natriuretic activity. The polypeptide can comprise a cGMP-activating property. The polypeptide can comprise a natriuretic and diuretic activity. The polypeptide can comprise a cardiac-unloading activity. The polypeptide can comprise an RAAS-suppressing activity. The polypeptide can lack the ability to induce systemic hypotension. The polypeptide can comprise the sequence set forth in SEQ ID NO:1. The polypeptide can comprise the sequence set forth in SEQ ID NO:6. The polypeptide can comprise the sequence set forth in SEQ ID NO:3. The polypeptide can comprise the sequence set forth in SEQ ID NO:1 with no more than three conservative amino acid substitutions (e.g., three, two, one, or no conservative amino acid substitutions). The polypeptide can comprise the sequence set forth in SEQ ID NO:6 with no more than five conservative amino acid substitutions (e.g., five, four, three, two, one, or no conservative amino acid substitutions). The polypeptide can comprise the sequence set forth in SEQ ID NO:3 with no more than three conservative amino acid substitutions (e.g., three, two, one, or no conservative amino acid substitutions). The host cell can be a eukaryotic host cell.

In another aspect, this document features a pharmaceutical composition comprising, or consisting essentially of, a pharmaceutically acceptable carrier and a polypeptide less than 44 amino acid residues in length, wherein the polypeptide comprises or consists essentially of, in an order from amino terminus to carboxy terminus:

(a) the sequence set forth in SEQ ID NO:1 or the sequence set forth in SEQ ID NO:1 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:3 or the sequence set forth in SEQ ID NO:3 with no more than three additions, subtractions, or substitutions, but which polypeptide is not a CD-NP polypeptide (SEQ ID NO:7). The polypeptide can comprise natriuretic activity. The polypeptide can comprise a cGMP-activating property. The polypeptide can comprise a natriuretic and diuretic activity. The polypeptide can comprise a cardiac-unloading activity. The polypeptide can comprise an RAAS-suppressing activity. The polypeptide can lack the ability to induce systemic hypotension. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise or consist essentially of the sequence set forth in SEQ ID NO:1, the sequence set forth in SEQ ID NO:2, and the sequence set forth in SEQ ID NO:3. The polypeptide can comprise the sequence set forth in SEQ ID NO:1 with no more than three conservative amino acid substitutions (e.g., three, two, one, or no conservative amino acid substitutions). The polypeptide can comprise the sequence set forth in SEQ ID NO:2 with no more than five conservative amino acid substitutions (e.g., five, four, three, two, one, or no conservative amino acid substitutions). The polypeptide can comprise the sequence set forth in SEQ ID NO:3 with no more than three conservative amino acid substitutions (e.g., three, two, one, or no conservative amino acid substitutions).

In another aspect, this document features a pharmaceutical composition comprising, or consisting essentially of, a pharmaceutically acceptable carrier and a polypeptide less than 44 amino acid residues in length, wherein the polypeptide comprises or consists essentially of, in an order from amino terminus to carboxy terminus:

(a) the sequence set forth in SEQ ID NO:1 or the sequence set forth in SEQ ID NO:1 with no more than three additions, subtractions, or substitutions, (b) the sequence set forth in SEQ ID NO:6 or the sequence set forth in SEQ ID NO:6 with no more than five additions, subtractions, or substitutions, and (c) the sequence set forth in SEQ ID NO:3 or the sequence set forth in SEQ ID NO:3 with no more than three additions, subtractions, or substitutions, but which polypeptide is not a CD-NP polypeptide (SEQ ID NO:7). The polypeptide can comprise natriuretic activity. The polypeptide can comprise a cGMP-activating property. The polypeptide can comprise a natriuretic and diuretic activity. The polypeptide can comprise a cardiac-unloading activity. The polypeptide can comprise an RAAS-suppressing activity. The polypeptide can lack the ability to induce systemic hypotension. The polypeptide can comprise the sequence set forth in SEQ ID NO:1. The polypeptide can comprise the sequence set forth in SEQ ID NO:6. The polypeptide can comprise the sequence set forth in SEQ ID NO:3. The polypeptide can comprise the sequence set forth in SEQ ID NO:1 with no more than three conservative amino acid substitutions (e.g., three, two, one, or no conservative amino acid substitutions). The polypeptide can comprise the sequence set forth in SEQ ID NO:6 with no more than five conservative amino acid substitutions (e.g., five, four, three, two, one, or no conservative amino acid substitutions). The polypeptide can comprise the sequence set forth in SEQ ID NO:3 with no more than three conservative amino acid substitutions (e.g., three, two, one, or no conservative amino acid substitutions).

In another aspect, this document features a method for increasing natriuretic activity within a mammal without lowering blood pressure. The method comprises, or consists essentially of, administering, to the mammal, a polypeptide less than 44 amino acid residues in length, wherein the polypeptide comprises or consists essentially of, in an order from amino terminus to carboxy terminus:

(a) the sequence set forth in SEQ ID NO:1 or the sequence set forth in SEQ ID NO:1 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:3 or the sequence set forth in SEQ ID NO:3 with no more than three additions, subtractions, or substitutions, but which polypeptide is not a CD-NP polypeptide (SEQ ID NO:7). The polypeptide can comprise natriuretic activity. The polypeptide can comprise a cGMP-activating property. The polypeptide can comprise a natriuretic and diuretic activity. The polypeptide can comprise a cardiac-unloading activity. The polypeptide can comprise an RAAS-suppressing activity. The polypeptide can lack the ability to induce systemic hypotension. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise or consist essentially of the sequence set forth in SEQ ID NO:1, the sequence set forth in SEQ ID NO:2, and the sequence set forth in SEQ ID NO:3. The polypeptide can comprise the sequence set forth in SEQ ID NO:1 with no more than three conservative amino acid substitutions (e.g., three, two, one, or no conservative amino acid substitutions). The polypeptide can comprise the sequence set forth in SEQ ID NO:2 with no more than five conservative amino acid substitutions (e.g., five, four, three, two, one, or no conservative amino acid substitutions). The polypeptide can comprise the sequence set forth in SEQ ID NO:3 with no more than three conservative amino acid substitutions (e.g., three, two, one, or no conservative amino acid substitutions). The polypeptide can be a substantially pure polypeptide.

In another aspect, this document features a method for increasing natriuretic activity within a mammal without lowering blood pressure. The method comprises, or consists essentially of, administering, to the mammal, a polypeptide less than 44 amino acid residues in length, wherein the polypeptide comprises or consists essentially of, in an order from amino terminus to carboxy terminus:

(a) the sequence set forth in SEQ ID NO:1 or the sequence set forth in SEQ ID NO:1 with no more than three additions, subtractions, or substitutions, (b) the sequence set forth in SEQ ID NO:6 or the sequence set forth in SEQ ID NO:6 with no more than five additions, subtractions, or substitutions, and (c) the sequence set forth in SEQ ID NO:3 or the sequence set forth in SEQ ID NO:3 with no more than three additions, subtractions, or substitutions, but which polypeptide is not a CD-NP polypeptide (SEQ ID NO:7). The polypeptide can comprise natriuretic activity. The polypeptide can comprise a cGMP-activating property. The polypeptide can comprise a natriuretic and diuretic activity. The polypeptide can comprise a cardiac-unloading activity. The polypeptide can comprise an RAAS-suppressing activity. The polypeptide can lack the ability to induce systemic hypotension. The polypeptide can comprise the sequence set forth in SEQ ID NO:1. The polypeptide can comprise the sequence set forth in SEQ ID NO:6. The polypeptide can comprise the sequence set forth in SEQ ID NO:3. The polypeptide can comprise the sequence set forth in SEQ ID NO:1 with no more than three conservative amino acid substitutions (e.g., three, two, one, or no conservative amino acid substitutions). The polypeptide can comprise the sequence set forth in SEQ ID NO:6 with no more than five conservative amino acid substitutions (e.g., five, four, three, two, one, or no conservative amino acid substitutions). The polypeptide can comprise the sequence set forth in SEQ ID NO:3 with no more than three conservative amino acid substitutions (e.g., three, two, one, or no conservative amino acid substitutions). The polypeptide can be a substantially pure polypeptide.

In another aspect, this document features a method for treating a mammal having a cardiovascular condition or renal condition. The method comprises, or consists essentially of, administering, to the mammal, a polypeptide under conditions wherein the severity of a manifestation of the cardiovascular condition or renal condition is reduced. The polypeptide is a polypeptide less than 44 amino acid residues in length, wherein the polypeptide comprises or consists essentially of, in an order from amino terminus to carboxy terminus:

(a) the sequence set forth in SEQ ID NO:1 or the sequence set forth in SEQ ID NO:1 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:3 or the sequence set forth in SEQ ID NO:3 with no more than three additions, subtractions, or substitutions, but which polypeptide is not a CD-NP polypeptide (SEQ ID NO:7). The polypeptide can comprise natriuretic activity. The polypeptide can comprise a cGMP-activating property. The polypeptide can comprise a natriuretic and diuretic activity. The polypeptide can comprise a cardiac-unloading activity. The polypeptide can comprise an RAAS-suppressing activity. The polypeptide can lack the ability to induce systemic hypotension. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise or consist essentially of the sequence set forth in SEQ ID NO:1, the sequence set forth in SEQ ID NO:2, and the sequence set forth in SEQ ID NO:3. The polypeptide can comprise the sequence set forth in SEQ ID NO:1 with no more than three conservative amino acid substitutions (e.g., three, two, one, or no conservative amino acid substitutions). The polypeptide can comprise the sequence set forth in SEQ ID NO:2 with no more than five conservative amino acid substitutions (e.g., five, four, three, two, one, or no conservative amino acid substitutions). The polypeptide can comprise the sequence set forth in SEQ ID NO:3 with no more than three conservative amino acid substitutions (e.g., three, two, one, or no conservative amino acid substitutions). The polypeptide can be a substantially pure polypeptide. Administration of the polypeptide to the mammal can lack the ability to lower the blood pressure of the mammal.

In another aspect, this document features a method for treating a mammal having a cardiovascular condition or renal condition. The method comprises, or consists essentially of, administering, to the mammal, a polypeptide under conditions wherein the severity of a manifestation of the cardiovascular condition or renal condition is reduced. The polypeptide is a polypeptide less than 44 amino acid residues in length, wherein the polypeptide comprises or consists essentially of, in an order from amino terminus to carboxy terminus:

(a) the sequence set forth in SEQ ID NO:1 or the sequence set forth in SEQ ID NO:1 with no more than three additions, subtractions, or substitutions, (b) the sequence set forth in SEQ ID NO:6 or the sequence set forth in SEQ ID NO:6 with no more than five additions, subtractions, or substitutions, and (c) the sequence set forth in SEQ ID NO:3 or the sequence set forth in SEQ ID NO:3 with no more than three additions, subtractions, or substitutions, but which polypeptide is not a CD-NP polypeptide (SEQ ID NO:7). The polypeptide can comprise natriuretic activity. The polypeptide can comprise a cGMP-activating property. The polypeptide can comprise a natriuretic and diuretic activity. The polypeptide can comprise a cardiac-unloading activity. The polypeptide can comprise an RAAS-suppressing activity. The polypeptide can lack the ability to induce systemic hypotension. The polypeptide can comprise the sequence set forth in SEQ ID NO:1. The polypeptide can comprise the sequence set forth in SEQ ID NO:6. The polypeptide can comprise the sequence set forth in SEQ ID NO:3. The polypeptide can comprise the sequence set forth in SEQ ID NO:1 with no more than three conservative amino acid substitutions (e.g., three, two, one, or no conservative amino acid substitutions). The polypeptide can comprise the sequence set forth in SEQ ID NO:6 with no more than five conservative amino acid substitutions (e.g., five, four, three, two, one, or no conservative amino acid substitutions). The polypeptide can comprise the sequence set forth in SEQ ID NO:3 with no more than three conservative amino acid substitutions (e.g., three, two, one, or no conservative amino acid substitutions). The polypeptide can be a substantially pure polypeptide. Administration of the polypeptide to the mammal can lack the ability to lower the blood pressure of the mammal.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 3 is an alignment of the primary structure of various natriuretic peptides shown with identical amino acids shaded.

DETAILED DESCRIPTION

Figure 1:
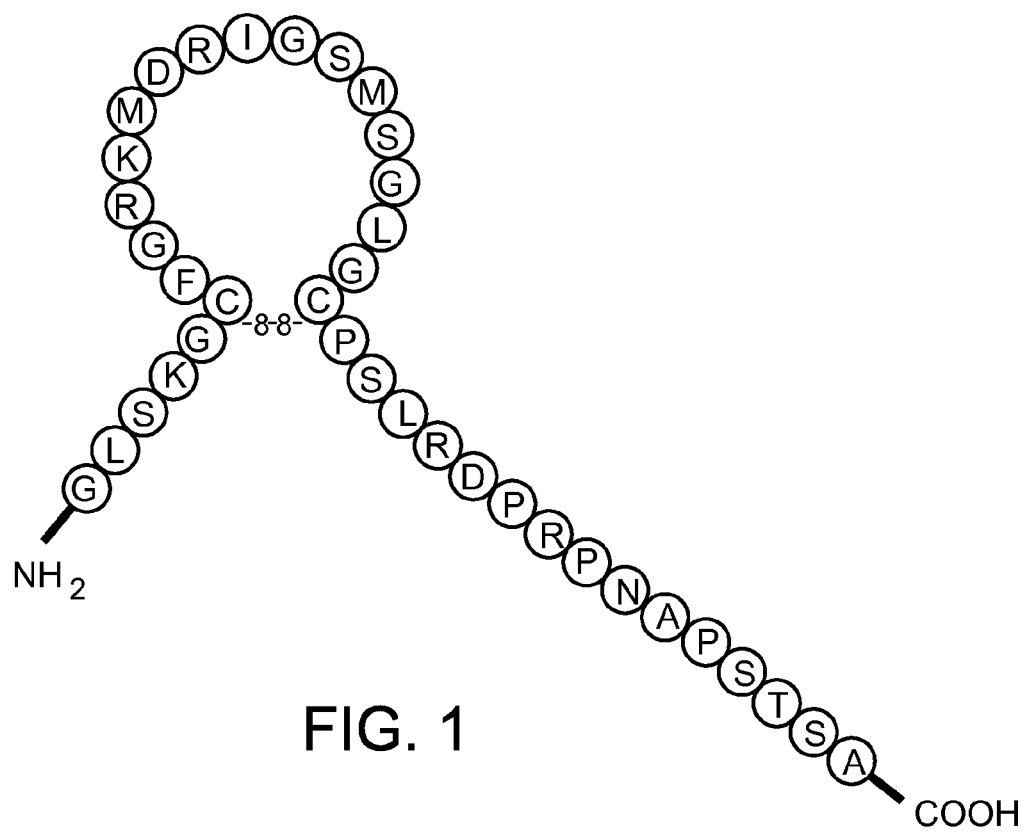
FIG. 1 is a schematic diagram of a B-CDNP polypeptide that is 37 amino acid residues in length (SEQ ID NO:4). The first five amino acid residues (SEQ ID NO:1) of SEQ ID NO:4 can be designated region 1. Amino acid residues 6 to 22 of SEQ ID NO:4 are set forth in SEQ ID NO:2 and can be designated as region 2. Amino acid residues 23 to 37 of SEQ ID NO:4 are set forth in SEQ ID NO:3 and can be designated as region 3.

This document relates to natriuretic polypeptides. For example, this document provides methods and materials related to natriuretic polypeptides and the use of natriuretic polypeptides to treat cardiovascular conditions (e.g., acute decompensated heart failure, acute coronary syndromes, and ventricular remodeling post-myocardial infarction) and renal conditions (e.g., perioperative renal dysfunction, renal dysfunction secondary to heart failure, and diabetic nephropathy).

In some cases, a polypeptide provided herein can have diuretic activity, natriuretic activity, the ability to activate cGMP, the ability to increase glomerular filtration rate, the ability to reduce renin production, the ability to reduce angiotensin production, the ability to reduce aldosterone production, the ability to reduce abnormally elevated cardiac filling pressures, the ability to optimize renal blood flow, or a combination thereof. In some cases, a polypeptide provided herein can increase endogenous ANP, BNP, and CNP levels. In some cases, a polypeptide provided herein can lack the ability to lower blood pressure or cause systemic hypotension. In some cases, a polypeptide provided herein can be an agonist for natriuretic peptide receptor-A, natriuretic peptide receptor-B, or both natriuretic peptide receptor-A and natriuretic peptide receptor-B.

A polypeptide provided herein can have any sequence. For example, a polypeptide provided herein can include the sequence set forth in SEQ ID NO:1, SEQ ID NO:2, and SEQ ID NO:3. In some cases, a polypeptide provided herein can contain an amino acid sequence that aligns to (a) the sequence set forth in SEQ ID NO:1 with three or less (e.g., two or less, one, or zero) amino acid additions, deletions, substitutions (e.g., conservative substitutions), or combinations thereof, (b) the sequence set forth in SEQ ID NO:2 with five or less (e.g., four or less, three or less, two or less, one, or zero) amino acid additions, deletions, substitutions (e.g., conservative substitutions), or combinations thereof, and (c) the sequence set forth in SEQ ID NO:3 with three or less (e.g., two or less, one, or zero) amino acid additions, deletions, substitutions (e.g., conservative substitutions), or combinations thereof. For example, a polypeptide provided herein can contain the sequence set forth in SEQ ID NO:1 with the exception that the first glycine residue or the last glycine residue of SEQ ID NO:1 is deleted or replaced with a different amino acid residue.

In some cases, a polypeptide provided herein can include the sequence set forth in SEQ ID NO:4. For example, a polypeptide provided herein can include the sequence set forth in SEQ ID NO:4 and no other amino acid residues. Such a polypeptide can include other non-amino acid residue components such as polysaccharides, lipids, acetyl groups, PEG, and methyl groups. In some cases, a polypeptide provided herein can include the sequence set forth in SEQ ID NO:4 with no more than eleven amino acid additions, deletions, substitutions (e.g., conservative substitutions), or combinations thereof (e.g., eleven, ten, nine, eight, seven, six, five, four, three, two, one, or zero amino acid additions, deletions, substitutions, or combinations thereof) provided that the polypeptide is not a CD-NP polypeptide (SEQ ID NO:7). Such a polypeptide can include the sequence set forth in SEQ ID NO:4 with no more than eleven amino acid additions, deletions, substitutions (e.g., conservative substitutions), or combinations thereof provided that the polypeptide includes the RKM amino acid sequence.

In some cases, a polypeptide provided herein can include the sequence set forth in SEQ ID NO:1, SEQ ID NO:6, and SEQ ID NO:3. In some cases, a polypeptide provided herein can contain an amino acid sequence that aligns to (a) the sequence set forth in SEQ ID NO:1 with three or less (e.g., two or less, one, or zero) amino acid additions, deletions, substitutions (e.g., conservative substitutions), or combinations thereof, (b) the sequence set forth in SEQ ID NO:6 with five or less (e.g., four or less, three or less, two or less, one, or zero) amino acid additions, deletions, substitutions (e.g., conservative substitutions), or combinations thereof, and (c) the sequence set forth in SEQ ID NO:3 with three or less (e.g., two or less, one, or zero) amino acid additions, deletions, substitutions (e.g., conservative substitutions), or combinations thereof. For example, a polypeptide provided herein can contain the sequence set forth in SEQ ID NO:1 with the exception that the first glycine residue or the last glycine residue of SEQ ID NO:1 is deleted or replaced with a different amino acid residue.

In some cases, a polypeptide provided herein can include the sequence set forth in SEQ ID NO:5. For example, a polypeptide provided herein can include the sequence set forth in SEQ ID NO:5 and no other amino acid residues. Such a polypeptide can include other non-amino acid residue components such as polysaccharides, lipids, acetyl groups, PEG, and methyl groups. In some cases, a polypeptide provided herein can include the sequence set forth in SEQ ID NO:5 with no more than eleven amino acid additions, deletions, substitutions (e.g., conservative substitutions), or combinations thereof (e.g., eleven, ten, nine, eight, seven, six, five, four, three, two, one, or zero amino acid additions, deletions, substitutions (e.g., conservative substitutions), or combinations thereof) provided that the polypeptide is not a CD-NP polypeptide (SEQ ID NO:7). Such a polypeptide can include the sequence set forth in SEQ ID NO:5 with no more than eleven amino acid additions, deletions, substitutions (e.g., conservative substitutions), or combinations thereof provided that the polypeptide includes the SSS amino acid sequence.

Amino acid substitutions can be conservative amino acid substitutions. Conservative amino acid substitutions can be, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitutions also include groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. After making an amino acid substitution, the activities of the polypeptide containing the amino acid substitution can be assessed using the assays described herein.

In some cases, a polypeptide provided herein can contain (a) a first amino acid sequence that either is set forth in SEQ ID NO:1 or aligns to the sequence set forth in SEQ ID NO:1 with three or less (e.g., two or less, one, or zero) amino acid deletions, substitutions (e.g., conservative substitutions), or combinations thereof, (b) a second amino acid sequence that either is set forth in SEQ ID NO:2 or aligns to the sequence set forth in SEQ ID NO:2 with five or less (e.g., four or less, three or less, two or less, one, or zero) amino acid additions, substitutions (e.g., conservative substitutions), or combinations thereof, and (a) a third amino acid sequence that either is set forth in SEQ ID NO:3 or aligns to the sequence set forth in SEQ ID NO:3 with three or less (e.g., two or less, one, or zero) amino acid deletions, substitutions (e.g., conservative substitutions), or combinations thereof. For example, a polypeptide provided herein can comprise or consist of the sequence set forth in SEQ ID NO:4.

In some cases, a polypeptide provided herein can contain (a) a first amino acid sequence that either is set forth in SEQ ID NO:1 or aligns to the sequence set forth in SEQ ID NO:1 with three or less (e.g., two or less, one, or zero) amino acid deletions, substitutions (e.g., conservative substitutions), or combinations thereof, (b) a second amino acid sequence that either is set forth in SEQ ID NO:6 or aligns to the sequence set forth in SEQ ID NO:6 with five or less (e.g., four or less, three or less, two or less, one, or zero) amino acid additions, substitutions (e.g., conservative substitutions), or combinations thereof, and (a) a third amino acid sequence that either is set forth in SEQ ID NO:3 or aligns to the sequence set forth in SEQ ID NO:3 with three or less (e.g., two or less, one, or zero) amino acid deletions, substitutions (e.g., conservative substitutions), or combinations thereof. For example, a polypeptide provided herein can comprise or consist of the sequence set forth in SEQ ID NO:5.

A polypeptide provided herein can have any length. For example, a polypeptide provided herein can be between 23 and 45 (e.g., between 25 and 45, between 26 and 44, between 27 and 43, between 28 and 42, between 29 and 41, between 30 and 40, between 31 and 39, between 23 and 35, between 25 and 30, or between 30 and 35) amino acid residues in length. It will be appreciated that a polypeptide with a length of 25 or 45 amino acid residues (i.e., a 25 or 45 amino acid polypeptide) is a polypeptide with a length between 25 and 45 amino acid residues.

In some cases, a polypeptide provided herein can be a substantially pure polypeptide. As used herein, the term "substantially pure" with reference to a polypeptide means that the polypeptide is substantially free of other polypeptides, lipids, carbohydrates, and nucleic acid with which it is naturally associated. Thus, a substantially pure polypeptide is any polypeptide that is removed from its natural environment and is at least 60 percent pure or is any chemically synthesized polypeptide. A substantially pure polypeptide can be at least about 60, 65, 70, 75, 80, 85, 90, 95, or 99 percent pure. Typically, a substantially pure polypeptide will yield a single major band on a non-reducing polyacrylamide gel.

A polypeptide provide herein can be obtained by expression of a recombinant nucleic acid encoding the polypeptide or by chemical synthesis (e.g., using solid phase polypeptide synthesis methods or an peptide synthesizer such as an ABI 431A Peptide Synthesizer; Applied Biosystems; Foster City, Calif.). For example, standard recombinant technology using expression vectors encoding a polypeptide provide herein can be used. The resulting polypeptides then can be purified using, for example, affinity chromatographic techniques and HPLC. The extent of purification can be measured by any appropriate method, including but not limited to: column chromatography, polyacrylamide gel electrophoresis, or high-performance liquid chromatography. A polypeptide provide herein can be designed or engineered to contain a tag sequence that allows the polypeptide to be purified (e.g., captured onto an affinity matrix). For example, a tag such as c-myc, hemagglutinin, polyhistidine, or Flag™ tag (Kodak) can be used to aid polypeptide purification. Such tags can be inserted anywhere within the polypeptide including at either the carboxyl or amino termini. Other fusions that can be used include enzymes that aid in the detection of the polypeptide, such as alkaline phosphatase.

A polypeptide provided herein can be produced to contain three regions, a first region that includes an N-terminus, a second region that includes a ring structure of a mature natriuretic polypeptide such as a human CNP polypeptide, and third region that includes a C-terminus. For example, a polypeptide provided herein can be produced to contain a first region that includes an N-terminus sequence from a human CNP polypeptide, a second region that includes a ring structure of a mature natriuretic polypeptide such as a human CNP or BNP polypeptide, and third region that includes a C-terminus sequence from a snake DNP polypeptide, but is not chimeric polypeptide CD-NP (SEQ ID NO:7).

A polypeptide provided herein can be used to treat cardiovascular diseases, congestive heart failure, myocardial infarction, coronary artery diseases, renal diseases, hepatic diseases, cancer, metabolic diseases, or combinations thereof. For example, a B-CDNP polypeptide having the amino acid sequence set forth in SEQ ID NO:4 or a CDNP-B polypeptide having the amino acid sequence set forth in SEQ ID NO:5 can be administered to a human having coronary artery disease under conditions wherein the severity of the human's coronary artery disease symptoms is reduced.

A polypeptide provided herein can be formulated as a pharmaceutical composition by admixture with pharmaceutically acceptable non-toxic excipients or carriers. Such compositions can be administered to a subject in need thereof in an amount effective to treat, for example, heart, liver, kidney, or other sodium retaining conditions. Pharmaceutical compositions can be prepared for parenteral administration, particularly in the form of liquid solutions or suspensions in aqueous physiological buffer solutions; for oral administration, particularly in the form of tablets or capsules; or for intranasal administration, particularly in the form of powders, nasal drops, or aerosols. Compositions for other routes of administration can be prepared as desired using appropriate methods.

Formulations for parenteral administration can include as common excipients, sterile water, saline, polyalkylene glycols such as polyethylene glycol, oils of vegetable origin, hydrogenated naphthalenes, and combinations thereof. In some cases, biocompatible, biodegradable lactide polymer, lactide/glycolide copolymer, polyoxethylene-polyoxypropylene copolymers, or combinations thereof can be used as excipients for controlling the release of the polypeptide in vivo. Other suitable parenteral delivery systems that can be used include, without limitation, ethylene-vinyl acetate copolymer particles, osmotic pumps, implantable infusion systems, liposomes, and combinations thereof. Formulations for inhalation administration can include excipients such as lactose. Inhalation formulations can be aqueous solutions containing, for example, polyoxyethylene-9-lauryl ether, glycocholate, deoxycholate, or combinations thereof, or they can be oily solutions for administration in the form of nasal drops. If desired, a composition containing a polypeptide provided herein can be formulated as gel to be applied intranasally. Formulations for parenteral administration can include glycocholate for buccal administration.

For oral administration, tablets or capsules can be prepared using appropriate methods with pharmaceutically acceptable excipients such as binding agents (e.g., pregelatinized maize starch, polyvinylpyrrolidone, or hydroxypropyl methylcellulose); fillers (e.g., lactose, microcrystalline cellulose or calcium hydrogen phosphate); lubricants (e.g. magnesium stearate, talc or silica); disintegrants (e.g., potato starch or sodium starch glycolate); or wetting agents (e.g., sodium lauryl sulfate). Tablets can be coated using appropriate methods. Preparations for oral administration can be formulated to give controlled release of the polypeptide.

Nasal preparations can be presented in a liquid form or as a dry product. Nebulised aqueous suspensions or solutions can include carriers or excipients to adjust pH and/or tonicity.

Nucleic Acids Encoding Polypeptides

This document also provides isolated nucleic acids that encode one or more of the polypeptides provided herein. The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid (e.g., a nucleic acid encoding a polypeptide comprising or consisting of the amino acid sequence set forth in SEQ ID NO:4 or SEQ ID NO:5) can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence. A nucleic acid existing among hundreds to millions of other nucleic acids within, for example, cDNA libraries or genomic libraries, or gel slices containing a genomic DNA restriction digest, is not to be considered an isolated nucleic acid.

As used herein, the term "nucleic acid" refers to both RNA and DNA, including mRNA, cDNA, genomic DNA, synthetic (e.g., chemically synthesized) DNA, and nucleic acid analogs. The nucleic acid can be double-stranded or single-stranded, and where single-stranded, can be the sense strand or the antisense strand. In addition, nucleic acid can be circular or linear. Nucleic acid analogs can be modified at the base moiety, sugar moiety, or phosphate backbone to improve, for example, stability, hybridization, or solubility of a nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered, morpholino ring, or peptide nucleic acids, in which the deoxyphosphate backbone is replaced by a pseudopeptide backbone and the four bases are retained. See, for example, Summerton and Weller *Antisense Nucleic Acid Drug Dev.*, 7:187-195 (1997); and Hyrup et al. *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotriester backbone.

A nucleic acid provided herein can comprise or consist of a sequence that encodes the amino acid sequence set forth in SEQ ID NO:4 or SEQ ID NO:5. For example, such a nucleic acid can contain the human nucleic acid sequence for CNP, BNP, and the snake nucleic acid sequence from DNP engineered to encode the amino acid sequence set forth in SEQ ID NO:4. In some cases, a nucleic acid can contain the human nucleic acid sequence for CNP, BNP, and the snake nucleic acid sequence from DNP, engineered to encode the amino acid sequence set forth in SEQ ID NO:5.

Typically, an isolated nucleic acid provided herein is at least 10 nucleotides in length (e.g., 10, 15, 20, 25, 30, 35, 40, 50, 75, 100, 200, 300, 350, 400, or more nucleotides in length). Nucleic acid molecules that are less than full-length can be useful, for example, as primers or probes for diagnostic purposes. Isolated nucleic acid molecules can be produced by standard techniques, including, without limitation, common molecular cloning and chemical nucleic acid synthesis techniques. For example, polymerase chain reaction (PCR) techniques can be used. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 15 to 50 nucleotides in length, but can range from 10 nucleotides to hundreds of nucleotides in length. For example, a primer can be 12, 15, 16, 17, 18, 19, 20, 21, 22, 23, 24, 25, 26, 27, 28, 29, 30, 35, 40, or 45 nucleotides in length. A primer can be purified from a restriction digest by conventional methods, or can be chemically synthesized. Primers typically are single-stranded for maximum efficiency in amplification, but a primer can be double-stranded. Double-stranded primers are first denatured (e.g., treated with heat) to separate the strands before use in amplification. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids as described elsewhere (Lewis, Genetic Engineering News, 12(9):1 (1992); Guatelli et al., *Proc. Natl. Acad. Sci. USA*, 87:1874-1878 (1990); and Weiss, *Science*, 254:1292 (1991)).

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids also can be obtained by mutagenesis. For example, a nucleic acid sequence encoding a polypeptide having the sequence set forth in SEQ ID NO:1, 2, 3, 4, 5, or 6 can be mutated using standard techniques such as, for example, oligonucleotide-directed mutagenesis and/or site-directed mutagenesis through PCR. See, *Short Protocols in Molecular Biology*, Chapter 8, Green Publishing Associates and John Wiley & Sons, Edited by Ausubel et al., 1992. Such mutations include additions, deletions, substitutions, and combinations thereof.

Vectors and Host Cells

This document also provides vectors containing a nucleic acid provided herein. As used herein, a "vector" is a replicon, such as a plasmid, phage, or cosmid, into which another DNA segment can be inserted so as to bring about the replication of the inserted segment. A vector can be an expression vector. An "expression vector" is a vector that includes one or more expression control sequences, and an "expression control sequence" is a DNA sequence that controls and regulates the transcription and/or translation of another DNA sequence.

In an expression vector provided herein, the nucleic acid can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it can be necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the polypeptide encoded by the coding sequence.

Suitable expression vectors include, without limitation, plasmids and viral vectors derived from, for example, bacteriophage, baculoviruses, tobacco mosaic virus, herpes viruses, cytomegalovirus, retroviruses, poxviruses, adenoviruses, and adeno-associated viruses. Numerous vectors and expression systems are commercially available from such corporations as Novagen (Madison, Wis.), Clontech Laboratories (Mountain View, Calif.), Stratagene (La Jolla, Calif.), and Invitrogen/Life Technologies (Carlsbad, Calif.).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide including at either the carboxyl or amino terminus.

This document also provides host cells containing a nucleic acid molecule and/or nucleic acid vector provided herein. The term "host cell" refers to prokaryotic cells and eukaryotic cells into which a nucleic acid molecule or vector can be introduced. Any method can be used to introduce nucleic acid into a cell. For example, calcium phosphate precipitation, electroporation, heat shock, lipofection, microinjection, and viral-mediated nucleic acid transfer can be used introduce nucleic acid into cells. In addition, naked DNA can be delivered directly to cells in vivo as described elsewhere (U.S. Pat. Nos. 5,580,859 and 5,589,466).

Detecting Polypeptides

This document provides methods and materials for detecting a polypeptide provided herein. Such methods and materials can be used to monitor polypeptide levels within a mammal receiving the polypeptide as a therapeutic. A polypeptide provided herein (e.g., a B-CDNP polypeptide having the amino acid sequence set forth in SEQ ID NO:4 or a CDNP-B polypeptide having the amino acid sequence set forth in SEQ ID NO:5) can be detected, for example, immunologically using one or more antibodies. As used herein, the term "antibody" includes intact molecules as well as fragments thereof that are capable of binding to an epitopic determinant of a polypeptide provided herein. The term "epitope" refers to an antigenic determinant on an antigen to which the paratope of an antibody binds. Epitopic determinants usually consist of chemically active surface groupings of molecules such as amino acids or sugar side chains, and typically have specific three-dimensional structural characteristics, as well as specific charge characteristics. Epitopes generally have at least five contiguous amino acids (a continuous epitope), or alternatively can be a set of noncontiguous amino acids that define a particular structure (e.g., a conformational epitope). The term "antibody" includes polyclonal antibodies, monoclonal antibodies, humanized or chimeric antibodies, single chain Fv antibody fragments, Fab fragments, and $F(ab)_2$ fragments. Polyclonal antibodies are heterogenous populations of antibody molecules that are contained in the sera of the immunized animals. Monoclonal antibodies are homogeneous populations of antibodies to a particular epitope of an antigen.

Antibody fragments that have specific binding affinity for a polypeptide provided herein (e.g., a B-CDNP polypeptide having the amino acid sequence set forth in SEQ ID NO:4 or a CDNP-B polypeptide having the amino acid sequence set forth in SEQ ID NO:5) can be generated by known techniques. For example, F(ab')2 fragments can be produced by pepsin digestion of the antibody molecule; Fab fragments can be generated by reducing the disulfide bridges of F(ab')2 fragments. In some cases, Fab expression libraries can be constructed. See, for example, Huse et al., *Science,* 246:1275 (1989). Once produced, antibodies or fragments thereof can be tested for recognition of a polypeptide provided herein by standard immunoassay methods including ELISA techniques, radioimmunoassays, and Western blotting. See, *Short Protocols in Molecular Biology*, Chapter 11, Green Publishing Associates and John Wiley & Sons, Edited by Ausubel, F. M et al., 1992.

In immunological assays, an antibody having specific binding affinity for a polypeptide provided herein or a secondary antibody that binds to such an antibody can be labeled, either directly or indirectly. Suitable labels include, without limitation, radionuclides (e.g. $^{125}I$, $^{131}I$, $^{35}S$, $^{3}H$, $^{32}P$, $^{33}P$, or $^{14}C$), fluorescent moieties (e.g., fluorescein, FITC, PerCP, rhodamine, or PE), luminescent moieties (e.g., Qdot™ nanoparticles supplied by Invitrogen (Carlsbad, Calif.)), compounds that absorb light of a defined wavelength, or enzymes (e.g., alkaline phosphatase or horseradish peroxidase). Antibodies can be indirectly labeled by conjugation with biotin then detected with avidin or streptavidin labeled with a molecule described above. Methods of detecting or quantifying a label depend on the nature of the label and are known in the art. Examples of detectors include, without limitation, x-ray film, radioactivity counters, scintillation counters, spectrophotometers, colorimeters, fluorometers, luminometers, and densitometers. Combinations of these approaches (including "multi-layer" assays) familiar to those in the art can be used to enhance the sensitivity of assays.

Immunological assays for detecting a polypeptide provided herein can be performed in a variety of known formats, including sandwich assays, competition assays (competitive RIA), or bridge immunoassays. See, for example, U.S. Pat. Nos. 5,296,347; 4,233,402; 4,098,876; and 4,034,074. Methods of detecting a polypeptide provided herein generally include contacting a biological sample with an antibody that binds to a polypeptide provided herein and detecting binding of the polypeptide to the antibody. For example, an antibody having specific binding affinity for a polypeptide provided herein can be immobilized on a solid substrate by any of a variety of methods known in the art and then exposed to the biological sample. Binding of the polypeptide to the antibody on the solid substrate can be detected by exploiting the phenomenon of surface plasmon resonance, which results in a change in the intensity of surface plasmon resonance upon binding that can be detected qualitatively or quantitatively by an appropriate instrument, e.g., a Biacore apparatus (Biacore International AB, Rapsgatan, Sweden). In some cases, the antibody can be labeled and detected as described above. A standard curve using known quantities of a polypeptide provided herein can be generated to aid in the quantitation of the levels of the polypeptide.

In some embodiments, a "sandwich" assay in which a capture antibody is immobilized on a solid substrate can be used to detect the presence, absence, or level of a polypeptide provided herein. The solid substrate can be contacted with the biological sample such that any polypeptide of interest in the sample can bind to the immobilized antibody. The presence, absence, or level of the polypeptide bound to the antibody can be determined using a "detection" antibody having specific binding affinity for the polypeptide. In some embodiments, a capture antibody can be used that has binding affinity for ANP, BNP, CNP, DNP, and CD-NP as well as a polypeptide provided herein. In this embodiment, a detection antibody can be used that has specific binding affinity for a particular polypeptide provided herein (e.g., a B-CDNP polypeptide having the amino acid sequence set forth in SEQ ID NO:4 or a CDNP-B polypeptide having the amino acid sequence set forth in SEQ ID NO:5). It is understood that in sandwich assays, the capture antibody should not bind to the same epitope (or range of epitopes in the case of a polyclonal antibody) as the detection antibody. Thus, if a monoclonal antibody is used as a capture antibody, the detection antibody can be another monoclonal antibody that binds to an epitope that is either physically separated from or only partially overlaps with the epitope to which the capture monoclonal antibody binds, or a polyclonal antibody that binds to epitopes other than or in addition to that to which the capture monoclonal antibody binds. If a polyclonal antibody is used as a capture antibody, the detection antibody can be either a monoclonal antibody that binds to an epitope that is either physically separated from or partially overlaps with any of the epitopes to which the capture polyclonal antibody binds, or a polyclonal antibody that binds to epitopes other than or in addition to that to which the capture polyclonal antibody binds. Sandwich assays can be performed as sandwich ELISA assays, sandwich Western blotting assays, or sandwich immunomagnetic detection assays.

Suitable solid substrates to which an antibody (e.g., a capture antibody) can be bound include, without limitation, microtiter plates, tubes, membranes such as nylon or nitrocellulose membranes, and beads or particles (e.g., agarose, cellulose, glass, polystyrene, polyacrylamide, magnetic, or magnetizable beads or particles). Magnetic or magnetizable particles can be particularly useful when an automated immunoassay system is used.

Antibodies having specific binding affinity for a polypeptide provided herein can be produced through standard methods. For example, a polypeptide can be recombinantly produced as described above, can be purified from a biological sample (e.g., a heterologous expression system), or can be chemically synthesized, and used to immunize host animals, including rabbits, chickens, mice, guinea pigs, or rats. For example, a polypeptide having the amino acid sequence set forth in SEQ ID NO:4 or SEQ ID NO:5, or fragments thereof that are at least six amino acids in length, can be used to immunize an animal. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol. Monoclonal antibodies can be prepared using a polypeptide provided herein and standard hybridoma technology. In particular, monoclonal antibodies can be obtained by any technique that provides for the production of antibody molecules by continuous cell lines in culture such as described by Kohler et al., Nature, 256:495 (1975), the human B-cell hybridoma technique (Kosbor et al., Immunology Today, 4:72 (1983); Cole et al., Proc. Natl. Acad. Sci. USA, 80:2026 (1983)), and the EBV-hybridoma technique (Cole et al., "Monoclonal Antibodies and Cancer Therapy," Alan R. Liss, Inc., pp. 77-96 (1983)). Such antibodies can be of any immunoglobulin class including IgG, IgM, IgE, IgA, IgD, and any subclass thereof. The hybridoma producing the monoclonal antibodies can be cultivated in vitro and in vivo.

Other techniques for detecting a polypeptide provided herein include mass-spectrophotometric techniques such as electrospray ionization (ESI), and matrix-assisted laser desorption-ionization (MALDI). See, for example, Gevaert et al., Electrophoresis, 22(9):1645-51 (2001); Chaurand et al., J. Am. Soc. Mass Spectrom., 10(2):91-103 (1999). Mass spectrometers useful for such applications are available from Applied Biosystems (Foster City, Calif.); Bruker Daltronics (Billerica, Mass.); and Amersham Pharmacia (Sunnyvale, Calif.).

The invention will be further described in the following examples, which do not limit the scope of the invention described in the claims.

EXAMPLES

Peptides and Reagents

A polypeptide with the sequence set forth in FIG. 1 was synthesized by Phoenix Pharmaceuticals, Inc. (Burlingame, Calif.). This polypeptide is referred to as a B-CDNP polypeptide (FIG. 1). Its molecular weight is 3808.44 and its amino acid sequence is Gly-Leu-Ser-Lys-Gly-Cys-Phe-Gly-Arg-Lys-Met-Asp-Arg-Ile-Gly-Ser-Met-Ser-Gly-Leu-Gly-Cys-Pro-Ser-Leu-Arg-Asp-Pro-Arg-Pro-Asn-Ala-Pro-Ser-Thr-Ser-Ala (SEQ ID NO:4) with a disulfide bridge joining the Cys residues.

Figure 2:
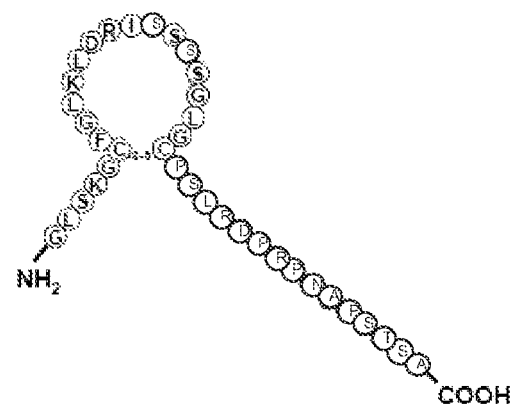
FIG. 2 is a schematic diagram of a CDNP-B polypeptide that is 37 amino acid residues in length (SEQ ID NO:5). The first five amino acid residues (SEQ ID NO:1) of SEQ ID NO:5 can be designated region 1. Amino acid residues 6 to 22 of SEQ ID NO:5 are set forth in SEQ ID NO:6 and can be designated as region 2. Amino acid residues 23 to 37 of SEQ ID NO:5 are set forth in SEQ ID NO:3 and can be designated as region 3.

A polypeptide with the sequence set forth in FIG. 2 was synthesized using by Phoenix Pharmaceuticals. This polypeptide is referred to as a CDNP-B polypeptide (FIG. 2). The synthesized CDNP-B polypeptide had a molecular weight of 3733.28, and its amino acid sequence Gly-Leu-Ser-Lys-Gly-Cys-Phe-Gly-Leu-Lys-Leu-Asp-Arg-Ile-Ser-Ser-Ser-Ser-Gly-Leu-Gly-Cys-Pro-Ser-Leu-Arg-Asp-Pro-Arg-Pro-Asn-Ala-Pro-Ser-Thr-Ser-Ala (SEQ ID NO:5) with a disulfide bridge joining the Cys residues.

Human ANP and CNP were purchased from Sigma (St. Louis, Mo.). Human BNP and DNP were synthesized by Phoenix Pharmaceuticals, Inc. CD-NP was manufactured by Clinalfa (Weil am Rhein, Germany). The lyophilized peptides were reconstituted in deionized water, aliquoted, and stored at −80° C. until used.

Cells

Human embryonic kidney 293 cells stably expressing rat or human NPR-A or NPR-B were maintained in Dulbecco's modified Eagle's medium (DMEM) supplemented with 10% FBS, 100 units/mL penicillin, 100 μg/mL streptomycin and 200 μg/mL G418 or hygromycin B.

Whole Cell cGMP Elevation Assays

Cells were plated in 48-well plates. The day of the assay, the cells were incubated in serum-free medium for 4 hours. The cells were incubated for 10 minutes at 37° C. in DMEM with medium containing 25 mM HEPES, pH 7.4 and 1 mM 1-methyl-3-isobutylxanthine (IBMX). This medium was then replaced with the same medium containing various concentrations of natriuretic peptides. The cells were stimulated for 1 or 3 minutes, and then the assay was terminated by aspirating the medium and adding 200 μL ice-cold 80% ethanol. Cyclic GMP concentrations were estimated by radioimmunoassay as described elsewhere (Abbey and Potter, *J. Biol. Chem.*, 277(45):42423-42430 (2002)).

Membrane Guanylyl Cyclase Assays

Crude membranes were prepared and assayed as described elsewhere (Bryan et al., *Am. J. Phys. Renal. Phys.*, 292(5): F1636-1644 (2007)). Briefly, cells from a 10-cm tissue culture plate were washed twice with ice-cold PBS and then scraped in cold buffer containing phosphatase inhibitors (PIB). The cells were lysed by sonicating 1 to 2 seconds, and membranes were precipitated by centrifugation. The crude membranes were resuspended in PIB buffer. Twenty microliters of membranes were assayed for 3 minutes at 37° C. containing 1 mM Mg-GTP in the presence or absence of various concentrations of natriuretic peptide. The assayed were stopped with the addition of 400 μL cold 50 mM sodium acetate buffer containing 5 mM EDTA and placed on ice. Cyclic GMP concentrations were determined on a fraction of the resulting solution by radioimmunoassay.

Whole Cell Binding Assays

Cells were plated on 24-well plates precoated with polylysine. When the cells were 75-90% confluent, the growth media was replaced with 0.2% BSA in DMEM. Cells were incubated for 1 to 2 hours in this media at 37° C. Binding media containing 1% BSA and $^{125}$I-ANP was prepared on ice. Binding media containing increasing concentrations of unlabelled ligand were added to the cells and incubated at 4° C. for 1 hour. The cells were washed with ice-cold PBS to remove non-specifically bound tracer. 0.5 mL of 1N NaOH was added to each well and incubated at room temperature to solubilize the cells. Radioactivity was determined in a Beckman gamma 5500 counter.

Statistics

Each experiment was performed in triplicate in three separate assays. The data were graphed with Prism software and presented as the average of all assays combined or as a representative experiment with vertical bars representing the standard error of the individual experiment.

Results

The following was performed to develop natriuretic peptide variants that are unique co-activators of NPR-B and NPR-A and, therefore, may have therapeutic advantage beyond native natriuretic peptides that are specific for NPR-B (CNP) or NPR-A (ANP and BNP) for the treatment of cardiorenal disease syndromes such as heart failure. The designed polypeptides can have the ability to reduce cardiac load, decrease cardiac remodeling, and enhance renal function.

Activation of human NPR-A. To unequivocally determine the ability of various ligands to activate human NPR-A (hNPR-A) or human NPR-B (hNPR-B), each individual receptor was stably expressed in human embryonic kidney 293 cells that are devoid of endogenous natriuretic peptide receptors. Using these cells, there was confidence that any increase in natriuretic peptide-dependent cGMP concentrations results from the activation of the single stably expressed receptor.

Figure 4A:
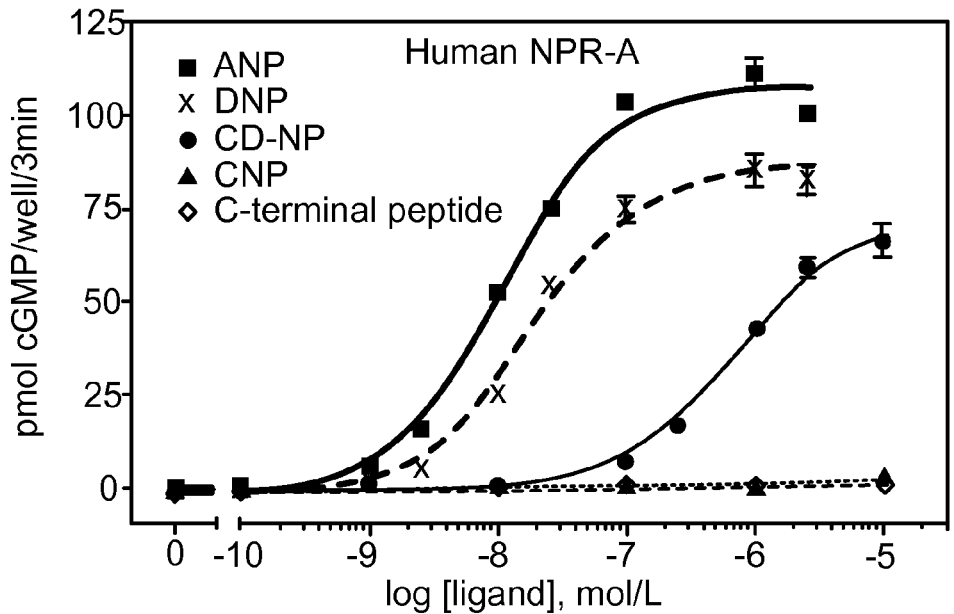
FIG. 4A is a graph plotting cellular cGMP concentration in response to activation of human NPR-A by CD-NP, CNP, ANP, and DNP polypeptides.

The ability of CD-NP to activate hNPR-A as compared to the original parent peptides, CNP or DNP, was tested first. Addition of the C-terminal portion of DNP to CNP resulted in a polypeptide that was a dramatically more potent activator of hNPR-A than CNP (FIG. 4A). While extremely high concentrations of CNP (10 μM) yielded just detectable increases in cellular cGMP concentrations, CD-NP produced equivalent responses at concentrations that were more than two orders of magnitude lower. The calculated $EC_{50}$ for CD-NP was 723 nM. Surprisingly, saturating concentrations of CD-NP produced significantly less cGMP elevations than saturating amounts of ANP, indicating that CD-NP is a partial agonist of hNPR-A. Because infusion of the linear C-terminal portion of DNP significantly increased urinary cGMP excretion in dogs, whether this same fragment could elevate cGMP levels in NPR-A expressing cells was tested. 10 M concentrations of this peptide did not elevate cGMP concentrations in cells expressing hNPR-A, consistent with previous studies showing that an intact ring structure is required for NPR-A activation.

Activation of Human NPR-B.

Figure 4B:
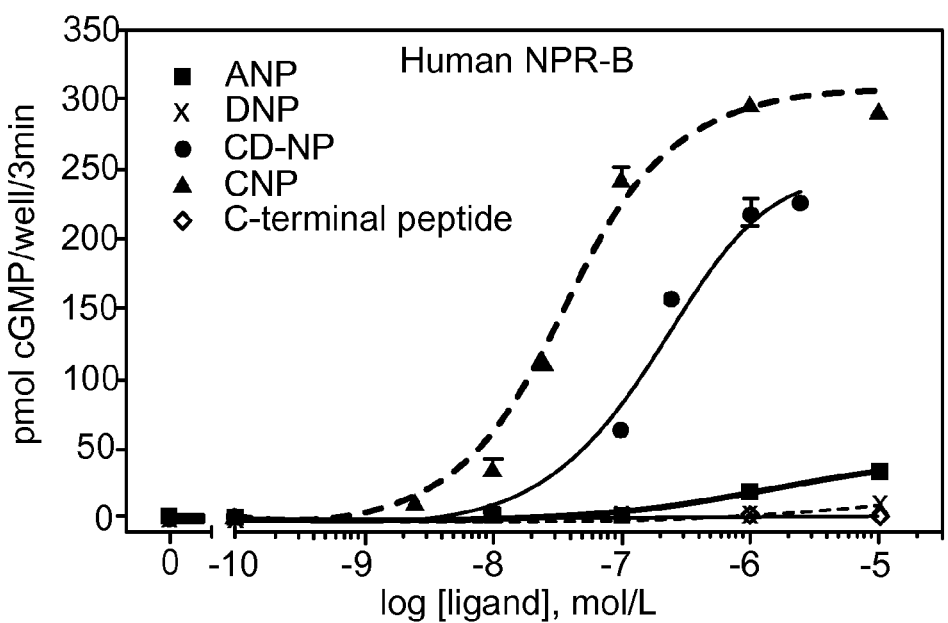
FIG. 4B is a graph plotting cellular cGMP concentration in response to activation of human NPR-B by CD-NP, CNP, ANP, and DNP polypeptides.

Similar experiments were conducted on 293 cells stably expressing hNPR-B. In these cells, CD-NP was about five-fold less potent than the natural ligand for NPR-B, CNP. The $EC_{50}$ for CD-NP was 202 nM compared to 38 nM for CNP (FIG. 4B). Hence, compared to CNP, CD-NP is a more than two hundred fold better agonist for NPR-A but a five fold worse agonist for NPR-B. Interestingly, the activity of CD-NP on NPR-B was much higher than the other NPR-A specific ligands, ANP and DNP, that contain residues C-terminal to the ring structure. As with hNPR-A, the linear C-terminal portion of DNP (C-terminal tail) was unable to stimulate hNPR-B (FIG. 4B).

Effect of CD-NP on Guanylyl Cyclase Activity.

Figure 5A:
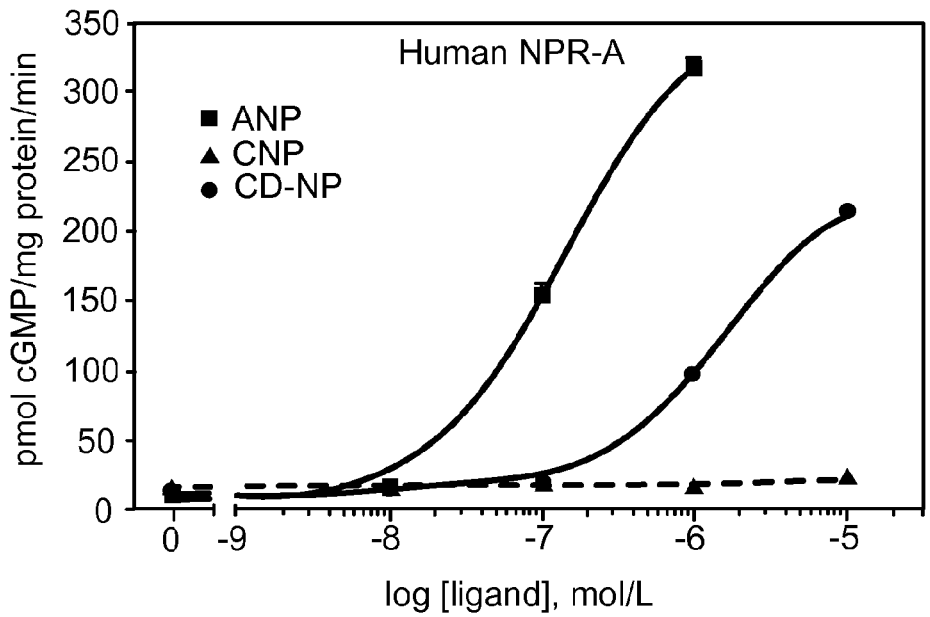
FIG. 5A is a graph plotting cellular cGMP concentration in response to activation of human NPR-A by ANP, CNP, and CD-NP polypeptides.
Figure 5B:
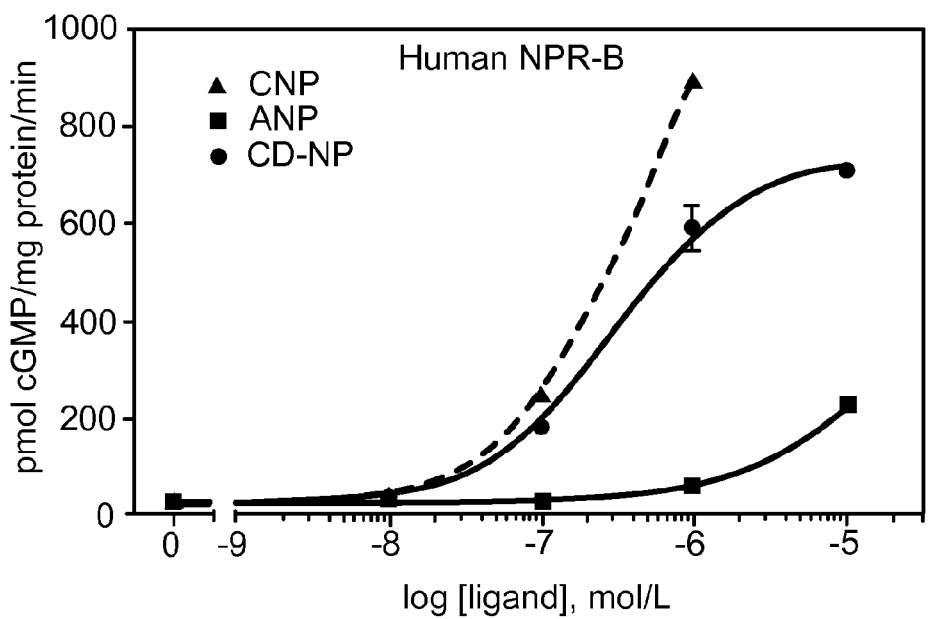
FIG. 5B is a graph plotting cellular cGMP concentration in response to activation of human NPR-B by CNP, ANP, and CD-NP polypeptides.

To determine if the cGMP elevations observed in whole cells were due to direct activation of the receptor by CD-NP, guanylyl cyclase assays were performed. Crude membranes prepared from HEK cells expressing hNPR-A or hNPR-B were incubated with 1 mM GTP and 5 mM $MgCl_2$ in the presence or absence of various concentrations of natriuretic peptide, and the amount of cGMP formed over a three minute period was determined (FIG. 5). Similar to the whole cell assays, CD-NP was a dramatically more potent activator of human NPR-A than CNP (FIG. 5A). In contrast, the addition of the DNP tail only slightly reduced the ability of CNP to activate hNPR-B (FIG. 5B).

Competition Binding of CD-NP in Human NPR-A Expressing Cells.

Figure 6A:
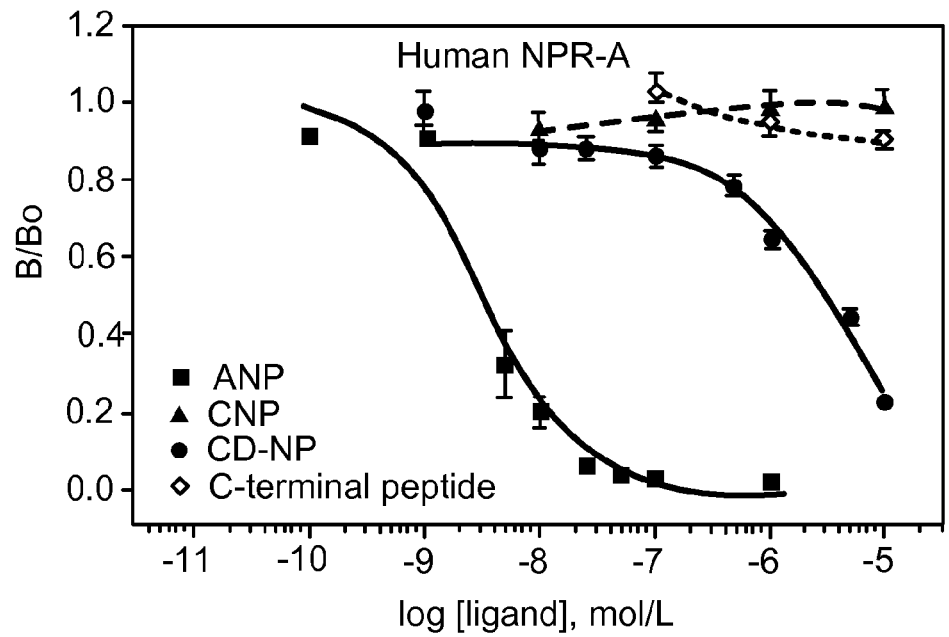
FIG. 6A is a graph plotting binding of ANP, CNP, CD-NP, and c-terminal peptide to human NPR-A.

To determine if the elevated sensitivity of hNPR-A to CD-NP was due to an increase in receptor binding affinity, competition $^{125}$I-ANP binding experiments were performed on whole hNPRA expressing 293 cells. CD-NP was not a particularly efficient competitor for binding to hNPR-A, since about 1000-fold more CD-NP than ANP was required to compete for $^{125}$I-ANP (FIG. 6A). However, much more striking was the complete inability of CNP or the C-terminal portion of DNP to compete for $^{125}$I-ANP binding to hNPR-A even at 10 µM concentrations. Hence, the addition of the carboxyl-terminal tail of DNP to the carboxyl-terminus of CNP dramatically increases its affinity for hNPR-A, consistent with the idea that CD-NP, but not CNP, is a NPR-A agonist. Similar experiments were attempted using $[^{125}$I$]$-[Tyr$_0$]CNP binding to hNPR-B. Unfortunately, the purchased tracer lacked the specificity necessary for accurate interpretation of the experiments.

Competition Binding of CD-NP in Human NPR-C Expressing Cells.

Figure 6B:
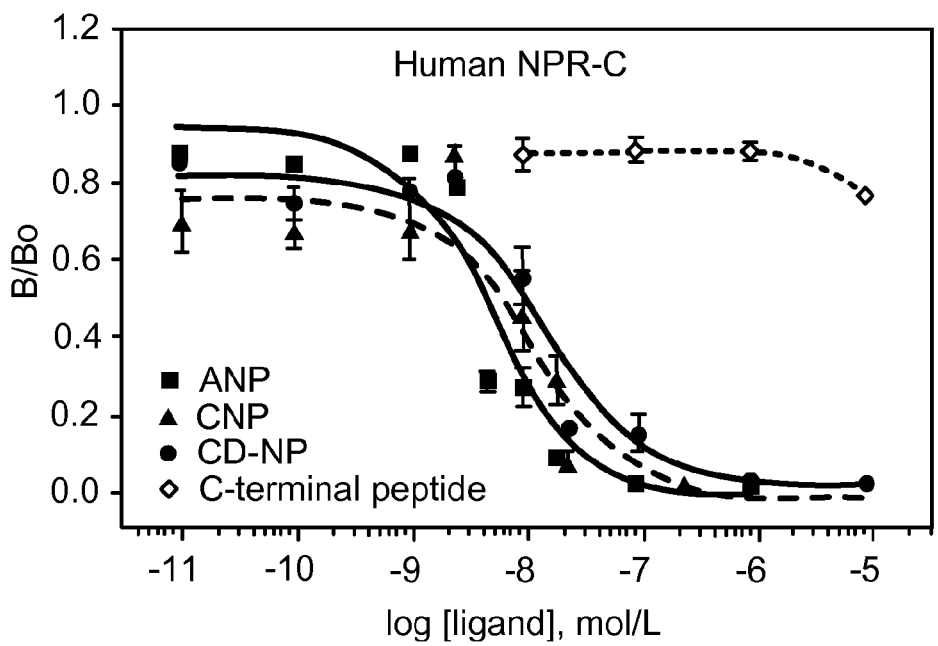
FIG. 6B is a graph plotting binding of ANP, CNP, CD-NP, and c-terminal peptide to human NPR-B.

The results provided herein indicate that CD-NP directly binds and activates hNPR-A. However, that does not necessary mean that the renal and hemodynamic effects of CD-NP result solely from the direct activation of hNPR-A. Another possible explanation is that infusion of CD-NP prolongs the half-life of endogenous ANP and/or BNP by competing for their degradation by the clearance receptor. To address this possibility, the ability of CD-NP, ANP, and CNP to compete for $^{125}$I-ANP binding to the clearance receptor was measured (FIG. 6B). In contrast to the dramatic effect that the DNP tail had on the ability of CNP to bind NPR-A, it had little, if any, effect on binding to NPR-C since similar concentrations of all three peptides were required to block binding of $^{51}$-ANP to this receptor. Thus, the addition of the C-terminal portion of DNP to CNP increases affinity to NPR-A, but not NPR-C.

Figure 6C:
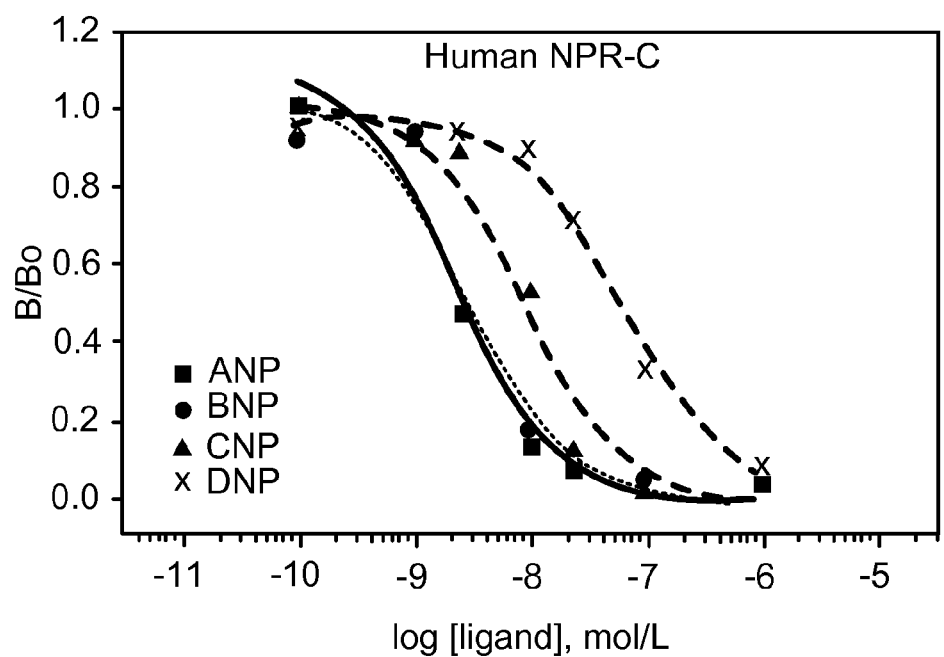
FIG. 6C is a graph plotting binding of ANP, BNP, CNP, and DNP to human NPR-C.

A previous report using $^{125}$I-DNP binding assays suggested that DNP does not bind NPR-C, whereas another group using $^{125}$I-ANP competition binding assays, concluded that DNP does bind NPR-C (Johns et al., Biochem. Biophys. Res. Comm., 358(1): 145-149 (2007)). To clarify this issue, the ability of DNP to displace $^{125}$I-ANP binding to NPR-C as compared to ANP, BNP, and CNP was tested. As shown in FIG. 6C, DNP binds 3-5 fold less avidly than CNP and 20 to 25-fold less avidly than ANP and BNP to the clearance receptor. Hence, these results resolve the debate in the literature concerning the ability of DNP to bind NPR-A versus NPR-C; it clearly does bind NPR-C, but it binds NPR-C less tightly than it binds NPR-A.

Activation of Rat Receptor Isoforms by CD-NP.

Figure 7A:
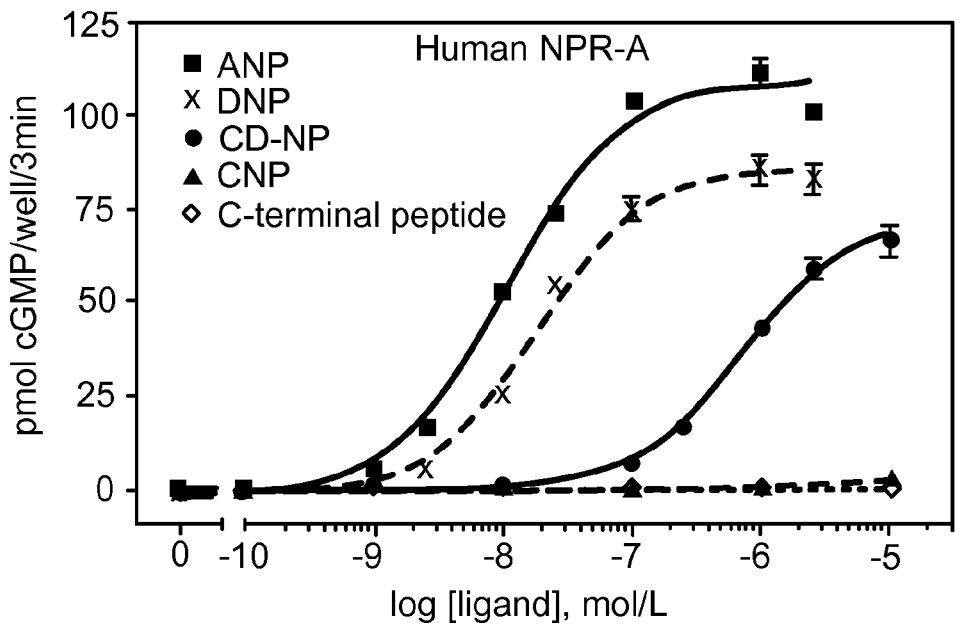
FIG. 7A is a graph plotting cellular cGMP concentration in response to activation of human NPR-A by ANP, DNP, CD-NP, CNP, and the c-terminal peptide.
Figure 7B:
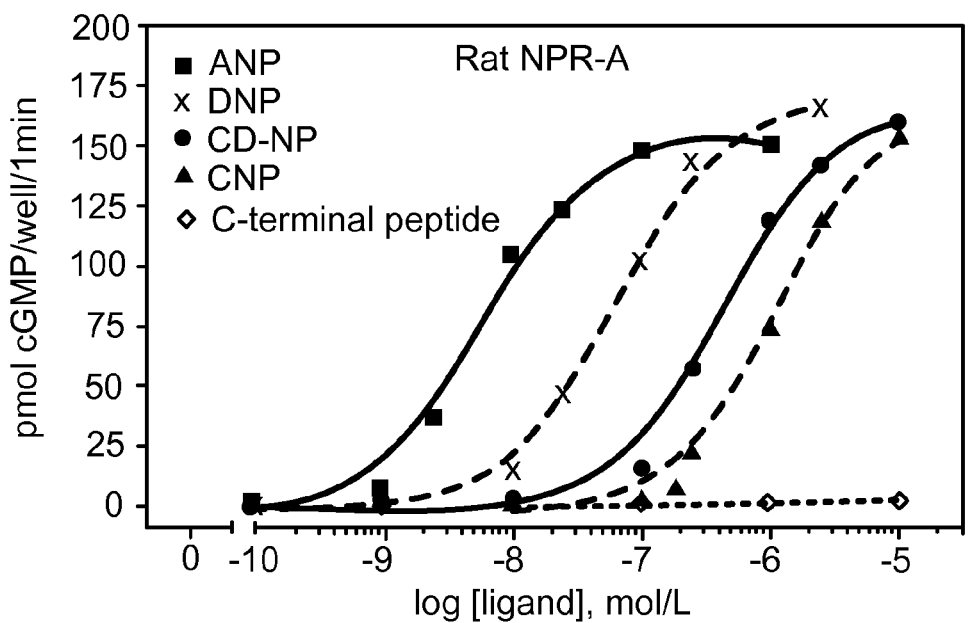
FIG. 7B is a graph plotting cellular cGMP concentration in response to activation of rat NPR-A by ANP, DNP, CD-NP, CNP, and the c-terminal peptide.

The ability of CD-NP to activate the rat versions of NPR-A and NPR-B was also determined. Here, two observations were made. First, unlike the human scenario where high concentrations of CNP had very little effect on hNPR-A (FIG. 7A), high concentrations of CNP were able to maximally activate rat NPR-A (FIG. 7B). Secondly, whereas CD-NP was a partial agonist of human NPR-A, it was a full agonist of rat NPR-A (FIG. 7B). In contrast, CD-NP had similar effects on rat and human NPR-B. Hence, the addition of the C-terminal tail of DNP to CNP has a greater effect on human NPR-A because this receptor is essentially unresponsive to CNP even at pharmacologic concentrations.

Effect of Amino Acid Substitutions within the CD-NP Ring.

Whether substitutions within the cysteine ring would lead to further increases in the EC$_{50}$ for hNPR-A activation was tested. Alignment of ANP, BNP, and CNP reveals four sections of amino acid divergence: the amino-terminus, a three amino acid segment just inside the first cysteine residue of the ring, a second three amino acid intra-ring sequence closer to the C-terminal cysteine, and the C-terminal tail (FIG. 3). The divergence of the C-terminal portions of the natriuretic peptides is addressed with the dramatic change in the pharmacological profile of CNP upon addition of the C-terminal portion of DNP. Previous studies tested the effect of adding the C-terminal tail of ANP (vasonatrin) or BNP to CNP, therefore, this region of the peptides is not addressed further. Instead, the focus was on modifications of the amino acids in the ring structure of CD-NP to further enhance its potency and/or affinity to human NPR-A. The corresponding sequence for BNP was substituted into the positions described above, and the effect of the modifications on the resultant peptides' abilities to activate the human natriuretic peptide receptors was measured. The mutations were based on BNP, not ANP, because BNP and NPR-A coevolved.

Figure 8A:
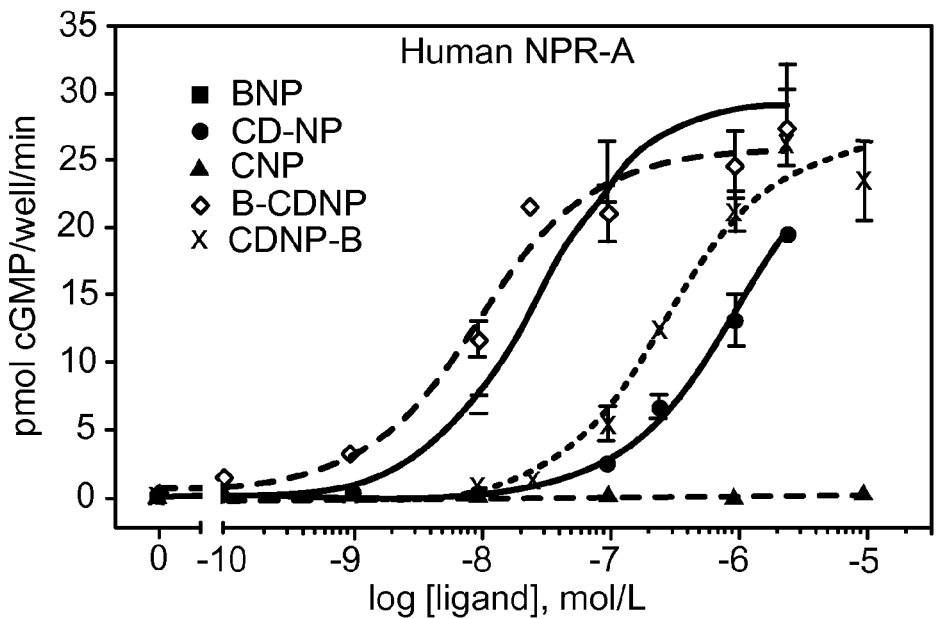
FIG. 8A is a graph plotting cellular cGMP concentration in response to activation of human NPR-A by BNP, CD-NP, CNP, B-CDNP, and CDNP-B.
Figure 8B:
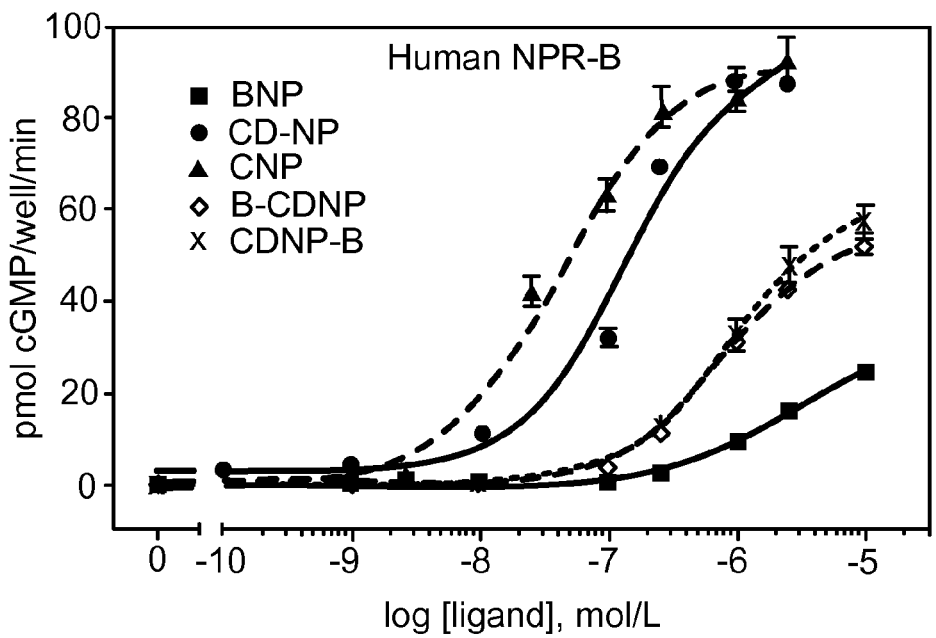
FIG. 8B is a graph plotting cellular cGMP concentration in response to activation of human NPR-B by BNP, CD-NP, CNP, B-CDNP, and CDNP-B.

The same assays that were used to characterize CD-NP were used to determine the ability of the new chimeric peptides to activate human NPR-A and NPR-B. However, in these studies, BNP was used rather than ANP as the representative NPR-A agonist since the sequence modifications for the new peptides were derived from BNP. ANP and BNP have similar abilities to activate NPR-A, although human ANP is typically a slightly better activator than BNP (EC$_{50}$=10.8 nM for ANP from FIG. 2 vs. EC$_{50}$=28.4 nM for BNP in FIG. 8A). As shown in FIG. 8A, the mutation of the first set of amino acids to comparable residues within BNP resulted in a dramatic leftward shift in the concentration of the peptide required to yield maximal cGMP elevations in NPR-A expressing cells. This peptide, which is called B-CDNP, was slightly more potent than human BNP; and unlike CD-NP, it was a full agonist. Mutation of the second set of amino acids within the ring structure of CNP to yield a peptide called CDNP-B also resulted in a peptide with increased full agonist potency over CD-NP, although the effect was much less dramatic. Both variants retained significant potency for NPR-B (FIG. 8B) since their EC$_{50}$'s for NPR-B were <1 µM, although the reduction in potency was greater than that observed for CD-NP.

Figure 9A:
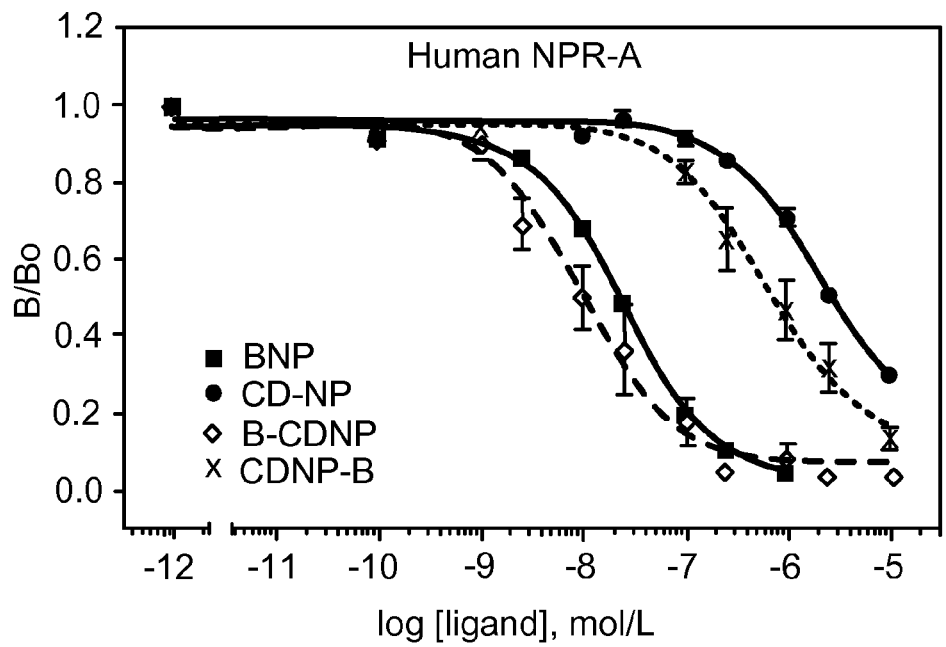
FIG. 9A is a graph plotting binding of BNP, CD-NP, B-CDNP, and CDNP-B to human NPR-A.
Figure 9B:
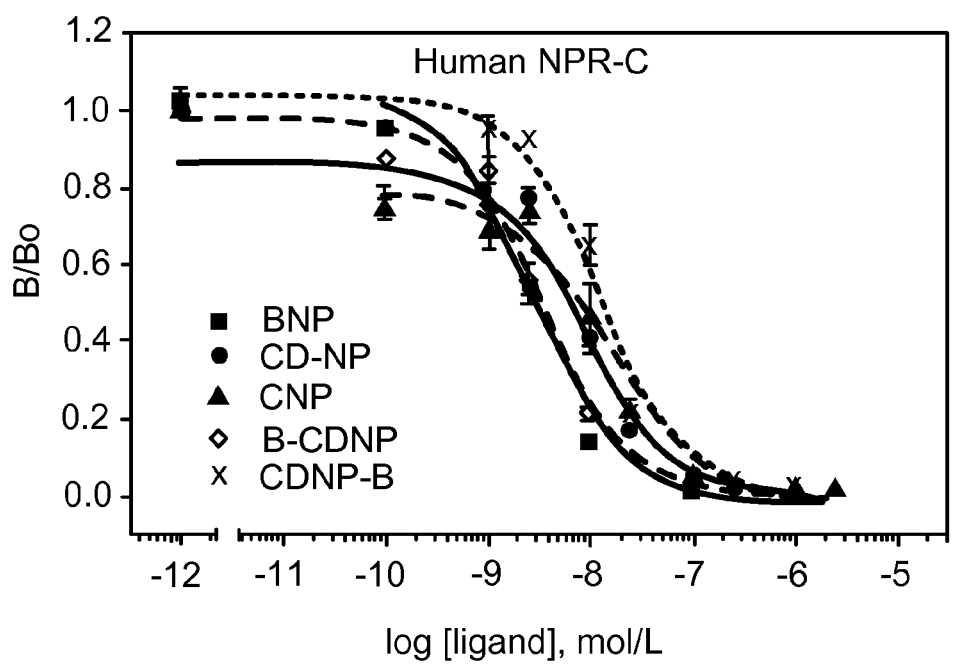
FIG. 9B is a graph plotting binding of BNP, CD-NP, B-CDNP, and CDNP-B to human NPR-B.

Competitive binding studies were conducted to determine if the change in potency of the CD-NP analogs verses CD-NP was due to increased affinity of the peptides for the extracellular domain of NPR-A. The binding profile shown in FIG. 9A was strikingly correlated with the whole cell receptor activation profile shown in FIG. 8A. Hence, the increased potency of the CD-NP analogs for NPR-A results from increased affinity for the receptor. The ring mutations are specific for NPR-A because they had minimal or no effect on the binding to NPR-C (FIG. 9B).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A polypeptide less than 44 amino acid residues in length, wherein said polypeptide comprises, in an order from amino terminus to carboxy terminus:
   (a) the sequence set forth in SEQ ID NO:1 or the sequence set forth in SEQ ID NO:1 with one addition, subtraction, or substitution,
   (b) the sequence set forth in SEQ ID NO:2 or the sequence set forth in SEQ ID NO:2 with one addition, subtraction, or substitution, and
   (c) the sequence set forth in SEQ ID NO:3 or the sequence set forth in SEQ ID NO:3 with one addition, subtraction, or substitution;
   wherein said polypeptide is not a CD-NP polypeptide consisting of the sequence set forth in SEQ ID NO:7, and wherein said polypeptide comprises natriuretic activity.

2. The polypeptide of claim 1, wherein said polypeptide comprises the sequence set forth in SEQ ID NO:1.

3. The polypeptide of claim 1, wherein said polypeptide comprises the sequence set forth in SEQ ID NO:2.

4. The polypeptide of claim 1, wherein said polypeptide comprises the sequence set forth in SEQ ID NO:3.

5. The polypeptide of claim 1, wherein said polypeptide comprises the sequence set forth in SEQ ID NO:1 with one addition, subtraction, or substitution.

6. The polypeptide of claim 1, wherein said polypeptide comprises the sequence set forth in SEQ ID NO:2 with one addition, subtraction, or substitution.

7. The polypeptide of claim 1, wherein said polypeptide comprises the sequence set forth in SEQ ID NO:3 with one addition, subtraction, or substitution.

8. The polypeptide of claim 1, wherein said polypeptide is a substantially pure polypeptide.

9. The polypeptide of claim 1, wherein said polypeptide comprises the sequence set forth in SEQ ID NO:1, the sequence set forth in SEQ ID NO:2, and the sequence set forth in SEQ ID NO:3.

* * * * *